(12) United States Patent
Keicher et al.

(10) Patent No.: US 7,157,434 B2
(45) Date of Patent: *Jan. 2, 2007

(54) NUCLEOSIDE COMPOUNDS FOR TREATING VIRAL INFECTIONS

(75) Inventors: Jesse D. Keicher, Menlo Park, CA (US); Christopher D. Roberts, Belmont, CA (US); Natalia B. Dyatkina, Mountain View, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/970,321

(22) Filed: Oct. 20, 2004

(65) Prior Publication Data

US 2005/0107312 A1 May 19, 2005

Related U.S. Application Data

(63) Continuation-in-part of application No. 10/861,090, filed on Jun. 4, 2004.

(60) Provisional application No. 60/602,815, filed on Aug. 18, 2004, provisional application No. 60/515,153, filed on Oct. 27, 2003.

(51) Int. Cl.
A61K 31/70 (2006.01)
C07H 19/14 (2006.01)

(52) U.S. Cl. .................. 514/43; 536/26.23; 536/26.26; 536/26.7; 536/27.2

(58) Field of Classification Search .................. 514/43; 536/26.23, 26.26, 26.7, 27.2
See application file for complete search history.

(56) References Cited

U.S. PATENT DOCUMENTS

| | | | |
|---|---|---|---|
| 4,140,851 A | 2/1979 | Townsend et al. | |
| 4,892,865 A | 1/1990 | Townsend et al. | |
| 4,927,830 A | 5/1990 | Townsend et al. | |
| 4,968,686 A | 11/1990 | Townsend et al. | |
| 5,681,941 A | 10/1997 | Cook et al. | |
| 5,763,597 A | 6/1998 | Ugarkar et al. | |
| 5,798,340 A | 8/1998 | Bischofberger et al. | |
| 5,811,534 A | 9/1998 | Cook et al. | |
| 5,824,796 A | 10/1998 | Petrie et al. | |
| 5,844,106 A | 12/1998 | Seela et al. | |
| 6,004,939 A | 12/1999 | Chen et al. | |
| 6,054,442 A | 4/2000 | Chen et al. | |
| 6,150,510 A | 11/2000 | Seela et al. | |
| 6,211,158 B1 | 4/2001 | Seela et al. | |
| 6,479,651 B1 | 11/2002 | Seela et al. | |
| 6,593,306 B1 | 7/2003 | Chen et al. | |
| 6,777,395 B1 | 8/2004 | Bhat et al. | |
| 7,094,768 B1 * | 8/2006 | Roberts et al. ............... 514/45 |
| 2002/0035077 A1 | 3/2002 | Tam et al. | |
| 2003/0096981 A1 | 5/2003 | Seela et al. | |
| 2003/0153744 A1 | 8/2003 | Mekouar et al. | |
| 2004/0014108 A1 | 1/2004 | Eldrup et al. | |
| 2004/0014957 A1 | 1/2004 | Eldrup et al. | |
| 2004/0067901 A1 | 4/2004 | Bhat et al. | |
| 2004/0072788 A1 | 4/2004 | Bhat et al. | |

FOREIGN PATENT DOCUMENTS

| | | |
|---|---|---|
| JP | 61-229897 | 10/1986 |
| WO | WO/1991/10671 | 7/1991 |
| WO | WO/1994/18215 | 8/1994 |
| WO | WO/1994/24144 | 10/1994 |
| WO | WO/1995/07919 | 3/1995 |
| WO | WO/1997/49833 | 12/1997 |
| WO | WO/2001/90121 | 5/2001 |
| WO | WO/2001/72764 | 10/2001 |
| WO | WO/2002/18404 | 3/2002 |
| WO | WO/2002/057287 | 7/2002 |
| WO | WO/2002/057425 | 7/2002 |
| WO | WO/2003/051899 | 6/2003 |
| WO | WO/2003/055896 | 7/2003 |
| WO | WO/2003/061576 | 7/2003 |
| WO | WO/2003/068244 | 8/2003 |
| WO | WO/2004/007512 | 1/2004 |
| WO | WO/2004/011478 | 2/2004 |
| WO | WO/2004/028481 | 4/2004 |
| WO | WO/2004/043977 | 5/2004 |

OTHER PUBLICATIONS

Bergstrom, et al. "Antiviral Activity of C-5 Substituted Tubercidin Analouges" *J. Med. Chem.* 27:285-292 (1984).

(Continued)

*Primary Examiner*—L. E. Crane
(74) *Attorney, Agent, or Firm*—Foley & Lardner LLP; Junrui Yang

(57) ABSTRACT

Disclosed are compounds, compositions and methods for treating viral infections caused by a flaviviridae family virus, such as hepatitis C virus. Such compounds are represented by Formula I as follows:

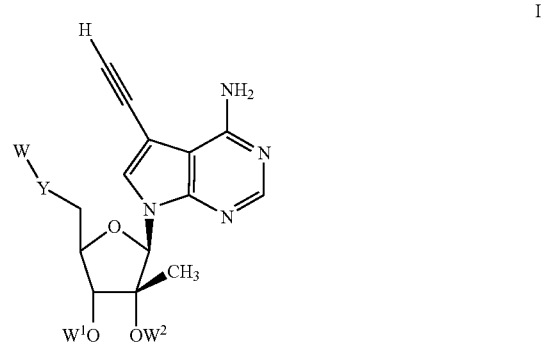

wherein, Y, W, $W^1$ and $W^2$ are as defined herein.

19 Claims, No Drawings

OTHER PUBLICATIONS

Hobbs, F.W. "alladium-Catalyzed Synthesis of Alkynylamino Nucleosides. A niversal Liner for Nucleic Acids" *J. Org. Chem.* 54:3420-3422 (1989).

DeClercq, et al. "Nucleic Acid Related Compounds. 51. Synthesis and Biological Properties of Sugar-Modified Analogues of the Nucleoside Antibiotics Tubercidin, Toyocamycin, Sangivamycin, and Formycin" *J. Med. Chem.* 30:481-486 (1987).

Bzowska et al., "7-Deazapurine 2'-deoxyribofuranosides are noncleavable competitive inhibitors of *Escherichia coli* purine nucleoside phosphorylase (PNP)," *Acta Biochimica Polonica*, 45(3):755-768 (1998).

Seela et al., "Pyrrolo[2,3d]Pyrididine Nucleosides: 7-Deaza-2'-Deoxyadenosines," *Nucleosides, Nucleotides & Nucleic Acids*, 19(1 &2):237-251 (2000).

Migliaccio et al., "Characterization of Resistance to Non-obligate Chain-terminating Ribonucleoside Analogs That Inhibit Hepatitis C Virus Replication in Vitro" *J.Biol.Chem.* 278(49):49164-49170 (2003).

Carroll et al., "Inhibition of Hepatitis C Virus RNA Replication by 2'-Modified Nucleoside Analogs" *J.Biol.Chem* 278(14):11979-11981(2003).

Seela et al, "Oligonucleoties containing 7-deazaadenines: the influence of the 7-substituent chain length and charge on the duplex stability," *Helvetica Cimica Acta.*, 82(11):1878-1898 (1999).

Rosemeyer, et al., "Stereoelectronic effects of modified purine bases on the sugar conformation of nucleosides: pyrrolo[2,3-d] pyrimidines," *Journal of the Chemical Society, Perkin Transactions 2: Physical Organic Chemistry*, 11:2341-2346 (1997).

Rosemeyer, et al., "Steric and stereoelectronic effects of 7-deazapurine bases on the sugar conformation of 2'-deoxynucleosides" *Nucleosides & Nucleotides* 16(7-9) 1447-1451 (1997).

Rosemeyer, et al., "Stereoelectronic effects of modified purines on the sugar conformation of nucleosides and fluorescence properties," *Nucleosides & Nucleotides* 16(5&6):821-828 (1997).

Seela, et al., "Palladium-catalyzed cross coupling of 7-iodo-2'-deoxytubercidin with terminal alkynes" *Synthesis* 6:726-730 (1996).

Schneller, et al., "Biological Activity and a modified synthesis of 8-Amino-3-β-D-ribofuranosyl-1,2,4-triazolo[4,3-a]pyrazine, and isomer of formycin," *J. Med Chem*. 27, 924-928 (1984).

Giziewicz, et al., "Antiviral and antimetabolic activities of formycin and its N-, N2-, 2'-O- and 3'-O-methylated derivatives," *Biochemical Pharmacology* 24, 1813-1817, (1975).

Bergstrom, et al., Pyrrolo[2,3-d]pyrimidine Nucleoside Antibiotic Analogues. Synthesis via Organopalladium Intermediates Derived from 5-Mercuritubercidin, *J. Org Chem*. 46:1423-1431 (1981).

Sharma, et al., "Synthesis of 5'-Substituted Derivatives of the Pyrrolo [2,3-d]-Pyrimidine Nucleoside Sangivamyin and their Effect on Protein Kinase A and C Activity," *Nucleosides & Nucleotides* 12(3&4) 295-304 (1993).

Müller, et al., "7-Deaza-2-phenyladenines: Structure-Activity Relationship of Potent A1 Selective Adenosine Receptor Antogonists" *J. Med. Chem*. 33:2822-2828 (1990).

Limori, et al., "2'-C-, 3'-C- and 5'-C-Methylsangivamycins: Conformational Lock With The Methyl Group," *Tetrahedrom Letters* 32(49) 7273-7276 (1991).

Kondo, et al., "Synthesis of 5-Methyltubercidin and Its α-Anomer via Condensation of the Anion of 4-Methoxy-5-methyl-2-methylthiopyrrolo [2, 3-d] pyrimidine and 2, 3,5-Tri-O-benzyl-D-ribofuranosyl Bromide," *Agric.Biol.Chem*.41(8):1501-1507 (1977).

Uematsu, et al., "5-Hydroxymethyltubercidin, Synthesis, Biological Activity, and Role in Pyrrolopyrimidine Biosynthesis," *J. of Med. Chem*, 16(12):1405-1407(1973).

Schram, et al., "Pyrrolopyrimidine Nucleosides VIII. Synthesis of Sangivamycin Derivatives possessing exocyclic heterocycles at C 5" *J. Carbohydrates, Nucleosides, Nucleotides* 1(1):39-54 (1974).

Murai et al. "A Synthesis and an X-Ray Analysis of 2'-C,3'-C- And 5'-C-Methylsangivamycins" *Heterocycles* 33:391-404 (1992).

Beigelman et al. "New Syntheses of 2'-C-Methylnucleosides Starting from D-Glucose and D-Ribose" *Carbo. Research*, 166:219-232 (1987).

\* cited by examiner

NUCLEOSIDE COMPOUNDS FOR TREATING VIRAL INFECTIONS

CROSS-REFERENCE TO RELATED APPLICATIONS

This application is a continuation-in-part of U.S. patent application Ser. No. 10/861,090 filed Jun. 4, 2004 which, in turn, claims the benefit under 35 U.S.C. § 119(e) of U.S. Provisional Patent Application Ser. No. 60/515,153 filed Oct. 27, 2003. The present application also claims the benefit under 35 U.S.C. § 119(e) of U.S. Provisional Patent Application Ser. No. 60/602,815 filed Aug. 18, 2004. All of these applications are incorporated herein by reference in their entirety.

BACKGROUND OF THE INVENTION

1. Field of the Invention

The invention relates to compounds for treating viral infections in mammals mediated, at least in part, by a virus in the flaviviridae family of viruses. This invention is also directed to pharmaceutical compositions and methods of use utilizing these compounds.

2. References

The following publications are cited in this application as superscript numbers:
1. Giangaspero, et al., Arch. Virol. Suppl., 7: 53–62 (1993);
2. Giangaspero, et al., Int. J. STD. AIDS, 4(5): 300–302 (1993);
3. Yolken, et al., Lancet, 1(8637): 517–20 (1989);
4. Wilks, et al., Lancet, 1(8629): 107 (1989);
5. Giangaspero, et al., Lancet, 2: 110 (1988);
6. Potts, et al., Lancet, 1(8539): 972–973 (1987);
7. Cornberg, et al., "Hepatitis C: therapeutic perspectives." Forum (Genova), 11(2):154–62 (2001);
8. Dymock, et al., Antivir. Chem. Chemother. 11(2):79–96 (2000);
9. Devos, et al., International Patent Application Publication No. WO 02/18404 A2, published 7 Mar. 2002;
10. Sommadossi, et al., International Patent Application Publication No. WO 01/90121, published 23 May, 2001;
11. Carroll, S. S., et al., International Patent Application Publication No. WO 02057287, published 25 Jul. 2002;
12. Carroll, S. S., et al., International Patent Application Publication No. WO 02057425, published 25 Jul. 2002;
13. Roberts, et al., U.S. patent application Ser. No. 10/861,090, filed Jun. 4, 2004.
14. Roberts, et al., U.S. patent application Ser. No. 10/861,311, filed Jun. 4, 2004.

All of the above publications and applications are herein incorporated by reference in their entirety to the same extent as if each individual publication or application was specifically and individually indicated to be incorporated by reference in its entirety.

State of the Art

The Flaviviridae family of viruses is composed of three genera: *pestivirus, flavivirus* and *hepacivirus* (hepatitis C virus). Of these genera, *flaviviruses* and *hepaciviruses* represent important pathogens of man and are prevalent throughout the world. There are 38 flaviviruses associated with human disease, including the dengue fever viruses, yellow fever virus and Japanese encephalitis virus. *Flaviviruses* cause a range of acute febrile illnesses and encephalitic and hemorrhagic diseases. Hepaciviruses currently infect approximately 2 to 3% of the world population and cause persistent infections leading to chronic liver disease, cirrhosis, hepatocellular carcinoma and liver failure. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients.[1-6]

Currently, there are no antiviral pharmaceutical drugs to prevent or treat pestivirus or flavivirus infections. For hepacivirus, i.e., hepatitis C virus (HCV) infections, interferon alpha (IFN) is currently the only approved drug in the United States. HCV is a major causative agent for post-transfusion and for sporadic non-A, non-B hepatitis. Infection by HCV is insidious in a high proportion of chronically infected (and infectious) carriers who may not experience clinical symptoms for many years.

At present, the only acceptable treatment for chronic HCV is interferon (IFN-alpha) and this requires at least six (6) months of treatment and/or ribavirin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1 H-1,2,-4-triazole-3-carboxamide), an inhibitor of inosine 5'-monophosphate dehydrogenase (IMPDH), enhances the efficacy of IFN-alpha in the treatment of HCV. Despite the introduction of Ribavirin, more than 50% of the patients do not eliminate the virus with the current standard therapy of interferon-alpha (IFN) and Ribavirin. By now, standard therapy of chronic hepatitis C has been changed to the combination of PEG-IFN plus ribavirin. However, a number of patients still have significant side effects, primarily related to Ribavirin. Ribavirin causes significant hemolysis in 10–20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection.

NS3/4A serine protease, ribonucleic acid (RNA) helicase, RNA-dependent RNA polymerase are considered as potential targets for new drugs.[7,8]

Devos, et al.[9] describes purine and pyrimidine nucleoside derivatives and their use as inhibitors of HCV RNA replication. Sommadossi, et al.[10] describes 1', 2' or 3'-modified nucleosides and their use for treating a host infected with HCV. Carroll, et al.[11,12], describes nucleosides as inhibitors of RNA-dependent RNA viral polymerase.

Recently, Roberts, et al.[13,14] disclosed that certain 7-(2'-substituted-β-D-ribofuranosyl)-4-amino-5-(optionally substituted ethyn-1-yl)-pyrrolo[2,3-d]pyrimidine compounds possess potent activity against HCV. These references are incorporated herein by reference in their entirety.

SUMMARY OF THE INVENTION

This invention is directed to novel compounds that are useful in the viral infections in mammals mediated, at least in part, by a virus in the flaviviridae family of viruses. Specifically this invention is directed to compounds of Formula I:

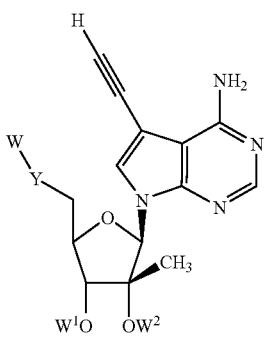

wherein
Y is selected from the group consisting of a bond, —CH$_2$— or —O—;
each of W, W$^1$ and W$^2$ is independently selected from the group consisting of hydrogen and a pharmaceutically acceptable prodrug; and
pharmaceutically acceptable salts or partial salts thereof.

In one preferred embodiment, Y is oxygen.

In another preferred embodiment each of W, W$^1$, and W$^2$ is independently hydrogen or a pharmaceutically acceptable prodrug selected from the group consisting of acyl, oxyacyl, phosphonate, phosphate, phosphate esters, phosphonamidate, phosphorodiamidate, phosphoramidate monoester, cyclic phosphoramidate, cyclic phosphorodiamidate, phosphoramidate diester, and —C(O)CHR$^2$NH$_2$ where R$^2$ is selected from the group consisiting of hydrogen, alkyl, substituted alkyl, aryl, substituted aryl, cycloalkyl, substituted cycloalkyl, heteroaryl, substituted hetereoaryl, heterocyclic and substituted heterocyclic. Preferably, R$^2$ is a sidechain of an amino acid. Preferably, W is hydrogen, or W$^1$ is hydrogen, or W$^2$ is hydrogen. More preferably, W and W$^1$ are hydrogen, or W and W$^2$ are hydrogen, or W$^1$ and W$^2$ are hydrogen. Even more preferably, W, W$^1$ and W$^2$ are hydrogen.

In still another preferred embodiment W$^1$ and W$^2$ are hydrogen and W is hydrogen or a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^2$NH$_2$.

In one particularly preferred embodiment, W$^1$ and W$^2$ are hydrogen and W is represented by the formula:

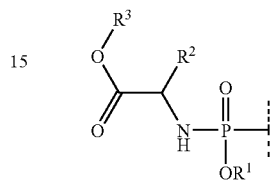

where R$^2$ is as defined above, R$^3$ is hydrogen or alkyl and R$^1$ is selected from the group consisting of alkyl, substutituted alkyl, aryl, substituted aryl, cycloalkyl, substituted cycloalkyl, heteroaryl, substituted heteroaryl, heterocyclic and substituted heterocyclic. In a preferred embodiment R$^2$ is derived from an L-amino acid.

In another particularly preferred embodiment, W and W$^2$ are hydrogen and W$^1$ is represented by the formula:

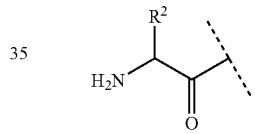

where R$^2$ is as defined above.

A particularly preferred aspect of this invention is directed to compounds of Formula II:

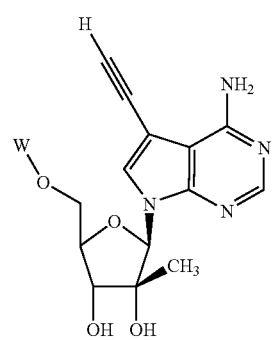

wherein
W is selected from the group consisting of hydrogen and a pharmaceutically acceptable prodrug;
or pharmaceutically acceptable salts or partial salts thereof.

Preferred compounds of this invention include those set forth in Table I below:

TABLE I
| # | Structure | Name |
|---|---|---|
| 101 | 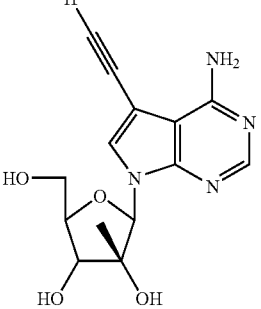 | 7-(2'-C-methyl-β-D-ribofuranosyl)-4-amino-5-(ethyn-1-yl)-pyrrolo[2,3-d]pyrimidine |
| 102 | 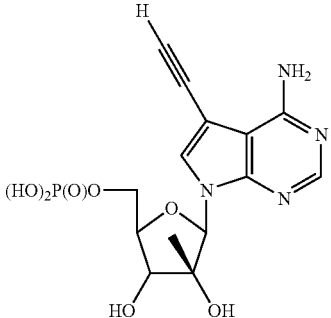 | 7-(2'-C-methyl-5'-phospho-α-D-ribofuranosyl)-4-amino-5-(ethyn-1-yl)-pyrrolo[2,3-d]pyrimidine |
| 103 | 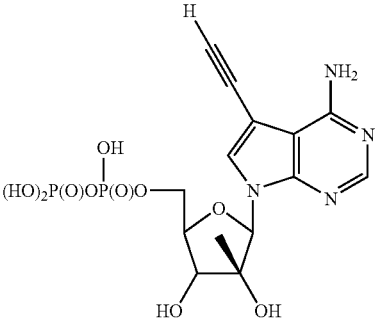 | 7-(2'-C-methyl-5'-diphospho-β-D-ribofuranosyl)-4-amino-5-[ethyn-1-yl]-pyrrolo[2,3-d]pyrimidine |
| 104 | 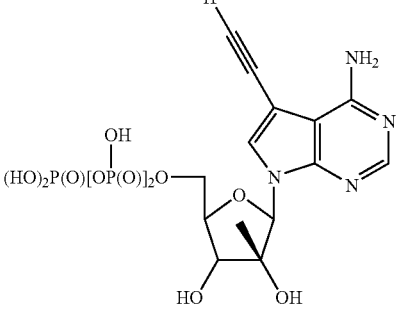 | 7-(2'-C-methyl-5'-triphospho-β-D-ribofuranosyl)-4-amino-5-(ethyn-1-yl)-pyrrolo[2,3-d]pyrimidine |

TABLE I-continued

| # | Structure | Name |
|---|---|---|
| 105 | 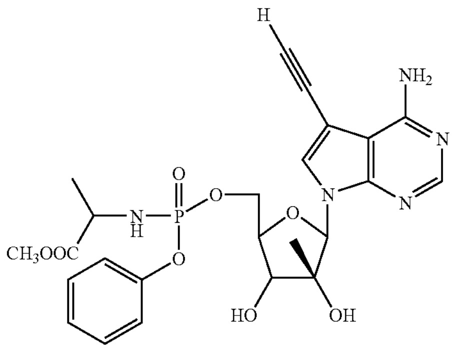 | 7-(2'-C-methyl-5'-(phenoxy-L-alaninyl)phosphate-β-D-ribofuranosyl)-4-amino-5-(ethyn-1-yl)-pyrrolo[2,3-d]pyrimidine |
| 106 | 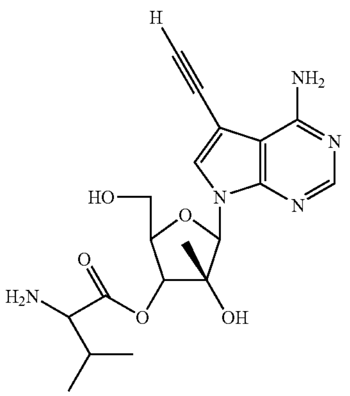 | 7-(2'-methyl-3'-O-L-valine ester-β-D-ribofuranosyl)-4-amino-5-(ethyn-1-yl)-pyrrolo[2,3-d]pyrimidine |
| 107 | 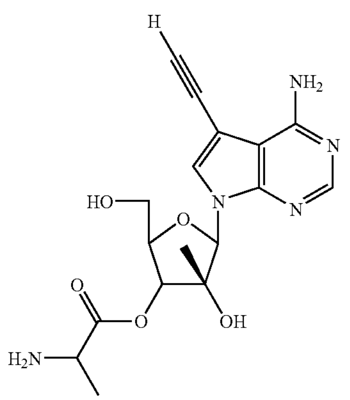 | 7-(2'-methyl-3'-O-L-alanin ester-β-D-ribofuranosyl)-4-amino-5-(ethyn-1-yl)-pyrrolo[2,3-d]pyrimidine (22b) |

Compounds of this invention are either active as antiviral agents or are useful as intermediates in the preparation of antiviral agents as described herein.

This invention is also directed to pharmaceutical compositions comprising a pharmaceutically acceptable diluent and a therapeutically effective amount of a compound as described herein or mixtures of one or more of such compounds.

This invention is still further directed to methods for treating a viral infection mediated at least in part by a virus in the flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of a compound as described herein or mixtures of one or more of such compounds.

In yet another embodiment of the invention, methods of treating or preventing viral infections in mammals are provided wherein the compounds of this invention are administered in combination with the administration of a therapeutically effective amount of one or more agents active against HCV. Active agents against HCV include ribavirin, levovirin, viramidine, thymosin alpha-1, an inhibitor of NS3 serine protease, and inhibitor of inosine monophosphate dehydrogenase, interferon-alpha or pegylated interferon-alpha, either alone or in combination with ribavirin or levovirin. Prefereably the additional agent active against HCV is interferon-alpha or pegylated interferon-alpha alone or in combination with ribavirin or levovirin.

DETAILED DESCRIPTION OF THE INVENTION

The invention is directed to compounds, compositions and methods for treating flaviviridae viruses, such as hepatitis C virus infections. However, prior to describing this invention in detail, the following terms will first be defined:

Definitions

As used herein, the term "alkyl" refers to alkyl groups having from 1 to 6 carbon atoms and more preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR$^4$R$^4$ where each R$^4$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^4$ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

"Alkenyl" refers to alkenyl group having from 2 to 6 carbon atoms and preferably 2 to 4 carbon atoms and having at least 1 and preferably from 1–2 sites of alkenyl unsaturation. Such groups are exemplified by vinyl (ethen-1-yl), allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the term "substituted alkenyl" includes both E (cis) and Z (trans) isomers as appropriate. The isomers can be pure isomeric compounds or mixtures of E and Z components.

"Alkynyl" refers to an unsaturated hydrocarbon having at least 1 site of alkynyl unsaturation and having from 2 to 6 carbon atoms and more preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR$^5$C(O)alkyl, —NR$^5$C(O)substituted alkyl, —NR$^5$C(O)cycloalkyl, —NR$^5$C(O)substituted cycloalkyl, —NR$^5$C(O)alkenyl, —NR$^5$C(O)substituted alkenyl, —NR$^5$C(O)alkynyl, —NR$^5$C(O)substituted alkynyl, —NR$^5$C(O)aryl, —NR$^5$C(O)substituted aryl, —NR$^5$C(O)heteroaryl, —NR$^5$C(O)substituted heteroaryl, —NR$^5$C(O)heterocyclic, and —NR$^5$C(O)substituted heterocyclic where R$^5$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl", including "substituted phenyl" refers to aryl groups or phenyl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings one or more of which may be aromatic or heteroaromatic provided that the point of attachment is through a cycloalkyl ring atom. Such groups include, by way of example, adamantyl, cyclopropyl, cyclobutyl, cyclopentyl, cyclooctyl and the like.

"Substituted cycloalkyl" refers to a saturated or unsaturated, but not aromatic, cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Formyl" refers to HC(O)—.

"Halo" or "halogen" refers to fluoro, chloro, bromo or iodo and preferably is fluoro or chloro.

"Heteroaryl" refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms, such as >N(O), >S(O) and >S(O)$_2$. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, thienyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, >S(O), and >S(O)$_2$ within the ring wherein, in fused ring systems, one or more of the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at, for example, the 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^6$) or salts thereof including partial salts thereof, wherein each R$^6$ is independently selected from hydrogen, alkyl, substituted alkyl, carboxyl, and carboxyl ester. It is understood, of course, that the initial oxygen of the phosphonate includes the oxygen atom at, for example, the 5-position of the ribose sugar.

"Phosphorodiamidate" refers to the group:

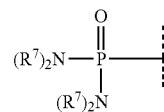

where each R$^7$ may be the same or different and each is hydrogen, alkyl, substituted alkyl, cycloalkyl, or substituted cycloalkyl. A particularly preferred phosphorodiamidate is the following group:

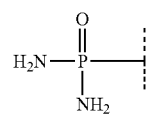

"Phosphoramidate monoester" refers to the group below, where R$^2$ and R$^3$ are as defined above. In a preferred embodiment R$^2$ is derived from an L-amino acid.

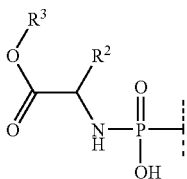

"Phosphoramidate diester" refers to the group below, where $R^1$, $R^2$ and $R^3$ are as defined above. In a preferred embodiment $R^2$ is derived from an L-amino acid.

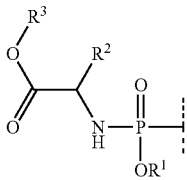

"Cyclic phosphoramidate" refers to the group below, where n is 1 to 3, more preferably n is 1 to 2.

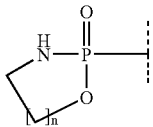

"Cyclic phosphorodiamidate" refers to the group below, where n is 1 to 3, more preferably n is 1 to 2.

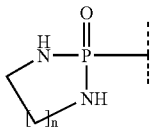

"Phosphonamidate" refers to the group below, where $R^{11}$ is hydrogen, alkyl, substituted alkyl, cycloalkyl, or substituted cycloalkyl.

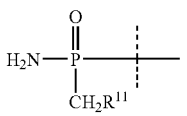

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid sidechain" refers to the $R^{12}$ substituent of α-amino acids of the formula $R^{13}NHCH(R^{12})COOH$ where $R^{12}$ is selected from the group consisting of hydrogen, alkyl, substituted alkyl and aryl and $R^{13}$ is hydrogen or together with $R^{12}$ and the nitrogen and carbon atoms bound thereto respectively form a heterocyclic ring. Preferably, the α-amino acid sidechain is the sidechain one of the twenty naturally occurring L amino acids.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The methods of this invention employ readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, the methods of this invention employ protecting groups which are necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, N.Y., 1999, and references cited therein.

Furthermore, the compounds of this invention contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1–15 (John Wiley and Sons, 1991), *Rodd's Chemistry of Carbon Compounds*, Volumes 1–5 and Supplementals (Elsevier Science Publishers, 1989), *Organic Reactions*, Volumes 1–40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides,*" Academic Press, New York, 1963; 2) Goodman L. "*Basic Principles in Nucleic Acid Chemistry,*" Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

The synthesis of the compounds of this invention generally follows either a convergent or linear synthetic pathway as described below. Scheme 1 below illustrates two different methods for preparing 7-(2'-methyl-β-D-ribofuranosyl)-4-amino-5-(ethyn-1-yl)-pyrrolo[2,3-d]pyrimidine

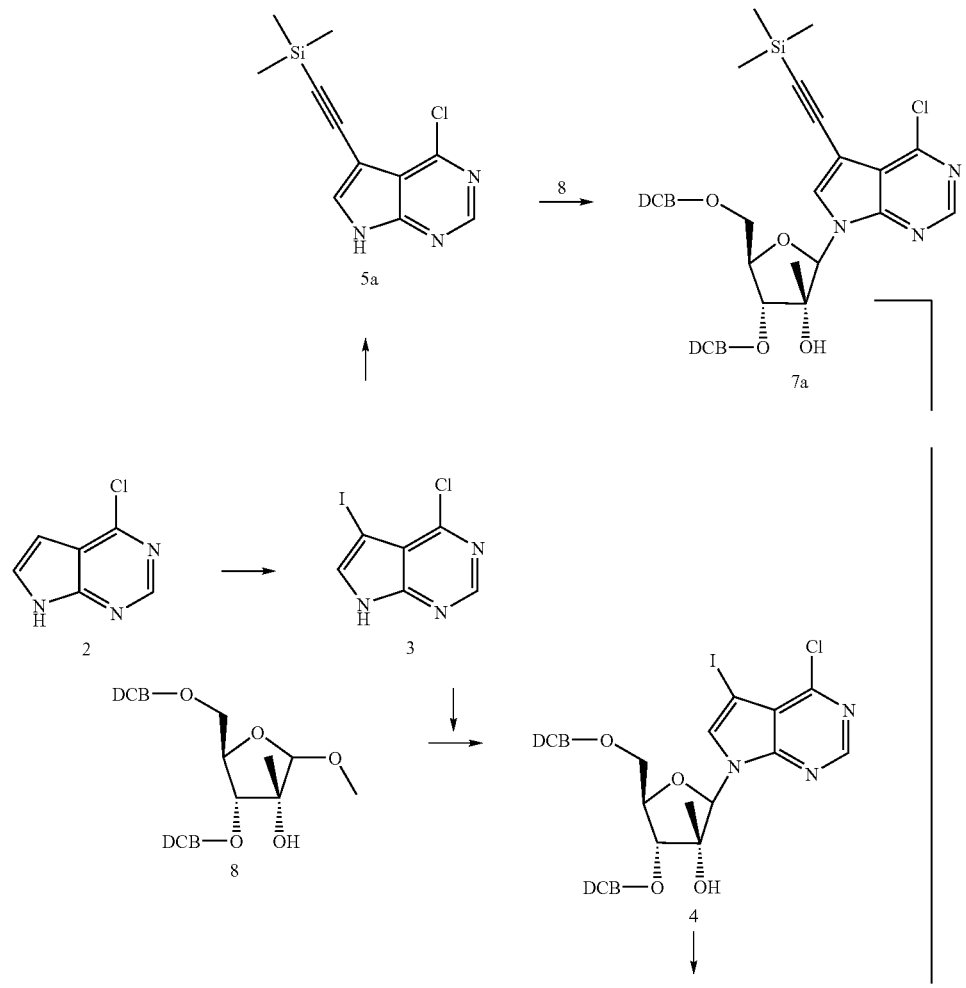

SCHEME 1

-continued

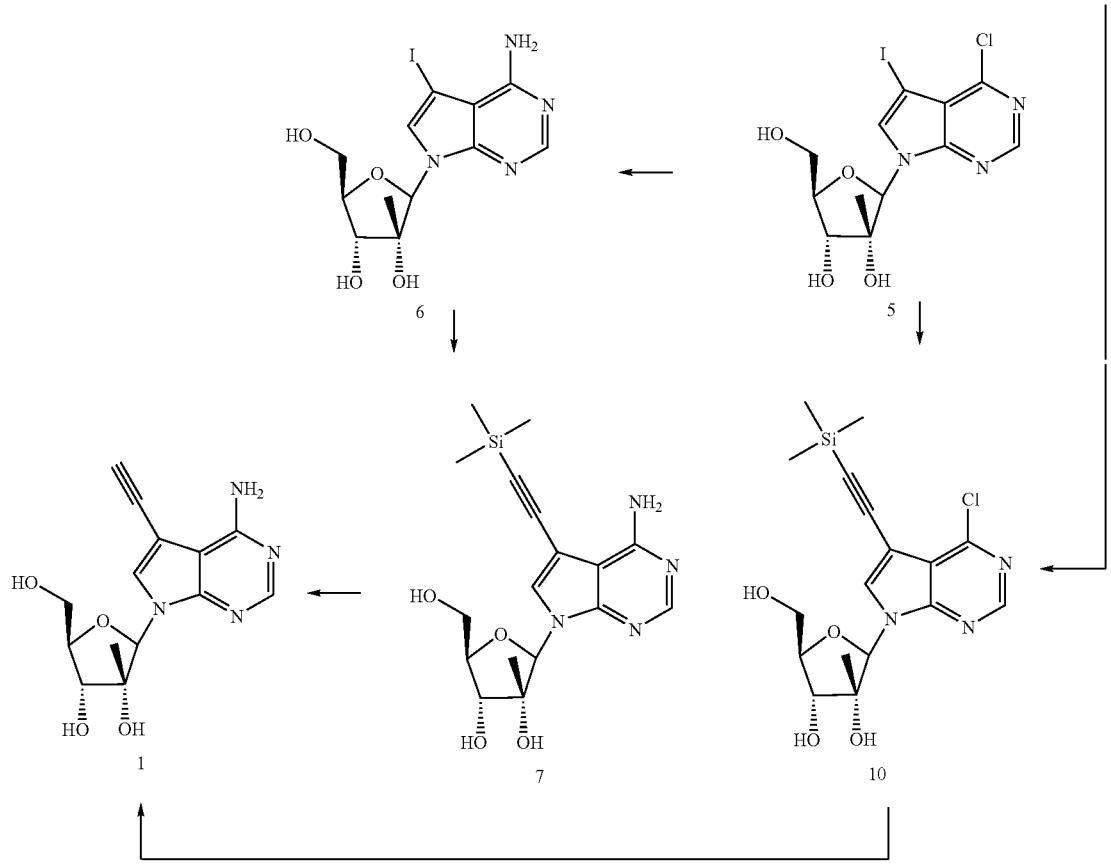

Specifically, in Scheme 1, commercially available 4-chloro-pyrrolo[2,3-d]pyrimidine, compound 2, is converted to the 4-chloro-5-iodo-pyrrolo[2,3-d]pyrimidine, compound 3, by contact with a slight excess and preferably from about 1.05 to 2 equivalents of N-iodo-succinimide in a suitable inert diluent such as DMF, acetonitrile, and the like. The reaction is typically conducted at from about 0° to about 40° C. and preferably at ambient conditions until substantial completion of the reaction. Preferably, the reaction is conducted in darkness (e.g., in a foil covered reaction chamber) and is typically completed within about 6 to 24 hours. The 4-chloro-5-iodo-pyrrolo[2,3-d]pyrimidine, compound 3, can be isolated by conventional methods such as filtration, evaporation and the like. Purification is preferably accomplished by crystallization with the yield of compound 3 being greater than 90 percent.

4-Chloro-5-iodo-pyrrolo[2,3-d]pyrimidine, compound 3, is combined into a suitable inert solvent such as acetonitrile, DMF, and the like at ambient conditions. A slight excess of sodium hydride, typically from about 1.01 to 1.1 and preferably about 1.04 equivalents relative to compound 3, is added portionwise to the solution. The resulting system is maintained with stirring at ambient conditions for a period of from about 0.5 to 4 hours and preferably for about 2 hours. Upon substantial completion of the reaction, any insoluble particles are removed from the reaction mixture by filtration. The sodium salt of compound 3 (not shown) in this filtrate is used in the next step without further purification.

Separately, 1-methoxy-2-methyl-3,5-di-O-(2,4-dichlorobenzyl)-D-ribofuranose, compound 8 (described below), is dissolved in a suitable inert diluent such as chloroform, methylene chloride, tetrahydrofuran and the like and the resulting system cooled to approximately 0° to 10° C. The corresponding 1-bromo-2-methyl-3,5-di-O-(2,4-dichlorobenzyl)-D-ribofuranose (not shown) is prepared in situ by reaction with gaseous hydrogen bromide which is bubbled through the reaction system until substantial completion of the reaction which typically occurs within 0.1 to 1 hour. The resulting product is obtained by evaporation, preferably at temperatures not exceeding 20° C. and residual traces of hydrogen bromide removed in vacuo (preferably at a pressure less than about 15 torr).

An excess, typically from about 1.01 to about 2 equivalents, (more preferably 1.5 to 2 eq) of the sodium salt of compound 3 is combined with 1-bromo-2-methyl-3,5-di-O-(2,4-dichlorobenzyl)-D-ribofuranose in a suitable solvent such as acetonitrile, DMF, and the like. Typically, the reaction is maintained at ambient conditions until substantially complete, which typically occurs within from about 6 to about 24 hours. The resulting product, 7-(2'-methyl-3',5'-di-O-(2,4-dichlorobenzyl)-β-D-ribofuranosyl)-4-chloro-5-iodo-pyrrolo[2,3-d]pyrimidine, compound 4, is isolated by conventional procedures. Preferably the reaction solution is neutralized and the solvent evaporated. Compound 4 is then triturated with a suitable solvent, for example, toluene, xylenes, and the like. The product can be purified by flash chromatography followed by crystallization.

Subsequently, the dichlorobenzyl protecting groups are removed by conventional procedures such as contacting 7-(2'-methyl-3',5'-di-O-(2,4-dichlorobenzyl)-β-D-ribofuranosyl)-4-chloro-5-iodo-pyrrolo[2,3-d]pyrimidine, compound 4, with BCl₃ to provide for 7-(2'-methyl-β-D-ribofuranosyl)-4-chloro-5-iodo-pyrrolo[2,3-d]pyrimidine, compound 5. Preferably, the reaction is conducted in an inert diluent such as chloroform, methylene chloride and the like. The reaction mixture is initially maintained at from about −60° to about −80° C. over a period of from about 1 to 4 hours and then allowed to warm to −40° to 0° C. until the reaction is substantially complete which typically occurs after an additional 1 to 24 hours. Afterwards the reaction is quenched with methanol and is then neutralized by raising the pH level to about 7, with a base, preferably with ammonium hydroxide. The resulting 7-(2'-methyl-β-D-ribofuranosyl)-4-chloro-5-iodo-pyrrolo[2,3-d]pyrimidine, compound 5, is isolated by conventional methods such as filtration, evaporation, chromatography, precipitation, and the like.

The 4-chloro group of compound 5 is then aminated by contact with an excess of liquid ammonia. The reaction is preferably conducted neat at a temperature of from about 75° to about 90° C. in a pressure reactor typically maintained at from about 100 to about 500 psi. The reaction is continued until substantial completion which typically occurs in about 12 to 48 hours. The resulting 7-(2'-methyl-β-D-ribofuranosyl)-4-amino-5-iodo-pyrrolo[2,3-d]pyrimidine, compound 6, is isolated by conventional methods such as filtration, evaporation, chromatography, precipitation, and the like.

As shown in Scheme 1, the iodo group of either the 7-(2'-methyl-β-D-ribofuranosyl)-4-chloro-5-iodo-pyrrolo[2,3-d]pyrimidine, compound 5, or the 7-(2'-methyl-β-D-ribofuranosyl)-4-amino-5-iodo-pyrrolo[2,3-d]pyrimidine, compound 6, is converted to the corresponding (trimethyl)silylacetylenyl group. Conversion is accomplished by first dissolving compound 5 or 6 in a suitable inert diluent such as DMF, THF or a mixture of DMF/THF such as 3:7 ratio. A catalytic amount of both cuprous iodide (CuI) and tetrakis(triphenylphosphine)palladium(0) is then added to the reaction mixture together with an excess, typically 1.1 to 2 equivalents, of (trimethylsilyl)acetylene. The reaction is preferably conducted in the presence of a base such as triethylamine and preferably is conducted under an inert atmosphere. The reaction is typically conducted at from about 10° to about 30° C. and is continued until substantial completion which typically occurs in about 12 to 48 hours.

The product derived from compound 5, i.e., 7-(2'-methyl-β-D-ribofuranosyl)-4-chloro-5-(trimethylsilylethynyl)pyrrolo[2,3-d]pyrimidine, compound 10, is isolated by conventional methods such as filtration, evaporation, chromatography, precipitation, and the like.

The product derived from compound 6, i.e., 7-(2'-methyl-β-D-ribofuranosyl)-4-amino-5-(trimethylsilyl-ethynyl)pyrrolo[2,3-d]pyrimidine, compound 7, is isolated by conventional methods such as filtration, evaporation, chromatography, precipitation, and the like.

Compound 7 can then be converted to the acetylene derivative (—C≡CH) by desilylation which occurs via conventional methods using ammonium hydroxide, potassium carbonate or fluoride anions. For example, reaction of 7-(2'-methyl-β-D-ribofuranosyl)-4-amino-5-(trimethylsilyl-ethynyl)pyrrolo[2,3-d]pyrimidine, compound 7, with ammonium hydroxide in methanol provides for compound 1.

Alternatively, desilylation and amination can be employed with compound 10 by reaction with concentrated ammonia to provide for compound 1.

In an alternative embodiment, compound 3 is first treated with a trimethylsilyl acetylene as described above to form compound 5a. Compound 5a may be coupled to 2'-methyl-3,5-di-O-(2,4-dichlorobenzyl)-D-ribofuranose as described above to form compound 7a. Finally removing the 2,4-dichlorobenzyl protecting groups from the sugar provides for compound 10.

Scheme 2 below illustrates synthetic variations in the preparation of 7-(2'-methyl-β-D-ribofuranosyl)-4-amino-5-(ethyn-1-yl)-pyrrolo[2,3-d]pyrimidine, compound 1.

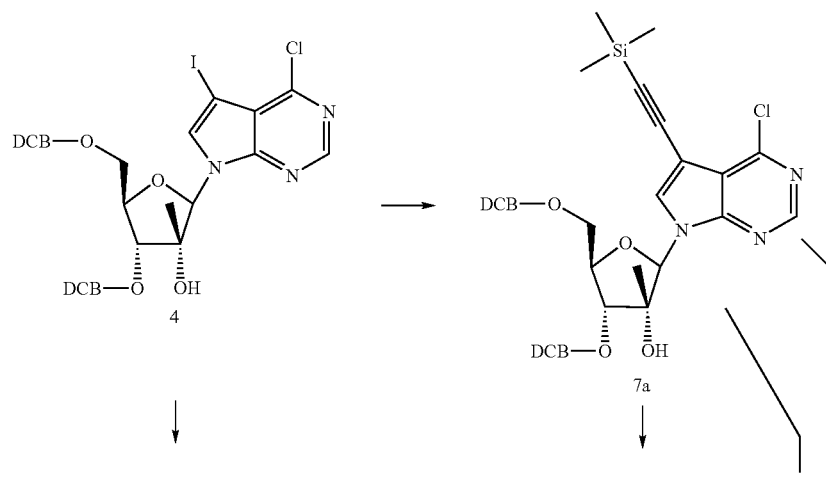

SCHEME 2

-continued

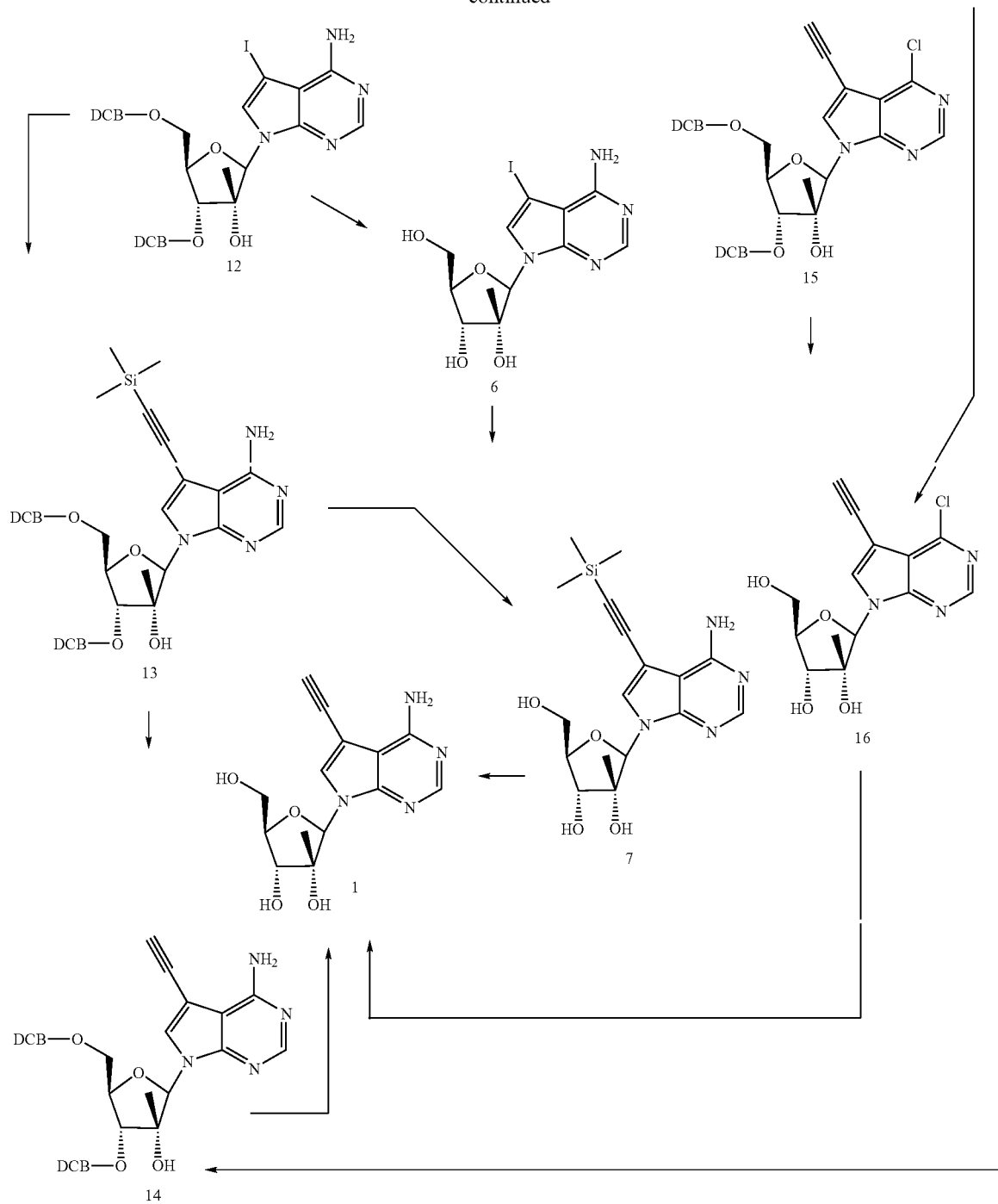

In Scheme 2, 7-(2'-methyl-3',5'-di-O-(2,4-dichlorobenzyl)-β-D-ribofuranosyl)-4-chloro-5-iodo-pyrrolo[2,3-d]pyrimidine, compound 4, is aminated in the methods as described above to provide for 7-(2'-methyl-3',5'-di-O-(2,4-dichlorobenzyl)-β-D-ribofuranosyl)-4-amino-5-iodo-pyrrolo[2,3-d]pyrimidine, compound 12. This compound serves as a focal point for a varity of reaction schemes which can be used to prepare 7-(2'-methyl-β-D-ribofuranosyl)-4-amino-5-(ethyn-1-yl)-pyrrolo[2,3-d]pyrimidine, compound 1.

In a first embodiment, the hydroxy protecting groups of compound 12 are removed using boron trichloride in the manner described in Scheme 1 above to provide for 7-(2'-methyl-β-D-ribofuranosyl)-4-amino-5-iodo-pyrrolo[2,3-d]pyrimidine, compound 6. Compound 6, in turn, is converted to the corresponding 7-(2'-methyl-β-D-ribofuranosyl)-4-amino-5-(trimethylsilylethynyl)-pyrrolo[2,3-d]pyrimidine, compound 7 using a catalytic amount of both cuprous iodide (CuI) and tetrakis(triphenyl-phosphine)palladium (0)

together with an excess, typically 1.1 to 2 equivalents, of (trimethylsilyl)acetylene in the presence of a base as described above.

In one embodiment, 7-(2'-methyl-β-D-ribofuranosyl)-4-amino-5-(trimethylsilyl-ethynyl)-pyrrolo[2,3-d]pyrimidine, compound 7 is desilylated as described above to provide for compound 1.

In another embodiment, compound 12 is converted to the corresponding 7-(2'-methyl-3',5'-di-O-(2,4-dichlorobenzyl)-β-D-ribofuranosyl)-4-amino-5-(trimethylsilylethynyl)-pyrrolo[2,3-d]pyrimidine, compound 13 using a catalytic amount of both cuprous iodide (CuI) and tetrakis(triphenylphosphine)palladium (0) together with an excess, typically 1.1 to 2 equivalents, of (trimethylsilyl)acetylene in the presence of a base as described above.

Compound 13 is subject to both desilylation and removal of the hydroxy protecting groups to provide for compound 1. As shown in Scheme 2, the order of these two steps is immaterial and in one embodiment, desilylation proceeds first in the manner described above to provide for 7-(2'-methyl-3',5'-di-O-(2,4-dichlorobenzyl)-β-D-ribofuranosyl)-4-amino-5-ethynyl-pyrrolo[2,3-d]pyrimidine, compound 14, which is then subject to removal of the hydroxy blocking groups, also as described above, to provide for compound 1. In another embodiment, removal of the hydroxy blocking groups proceeds first to provide for 7-(2'-methyl-β-D-ribofuranosyl)-4-amino-5-(trimethylsilyl-ethynyl)-pyrrolo[2,3-d]pyrimidine, compound 7 which is then subject to desilylation to provide for compound 1.

Alternatively, compound 7a can be prepared by reacting compound 4 with a trimethylsilyl acetylene as described above. The trimethylsilyl group of compound 7a can be removed as described above to provide for compound 15. Compound 16 is prepared by removal of the benzyl protecting groups from compound 15. Amination of compound 15 using techniques described above provides for compound 1.

In another alternative process, compound 7a can be converted directly to compound 14 by aminating with liquid ammonia.

The 2-substituted ribose sugars used in Schemes 1 and 2 above can be prepared from methods well known in the art. For example, one starting material of these compounds is an appropriately substituted sugar with 2'-OH and 2'-H. The sugar can be purchased or can be prepared by any known means including standard epimerization, substitution, oxidation and/or reduction techniques. For example, commercially available 1,3,5-tri-O-benzoyl-α-D-ribofuranose (Pfanstiel Laboratories, Inc.) can be used. The substituted sugar can then be oxidized with the appropriate oxidizing agent in a compatible solvent at a suitable temperature to yield the 2'-modified sugar. Possible oxidizing agents are, for example, Dess-Martin periodine reagent, $Ac_2O$+ DCC in DM50, Swern oxidation (DMSO, oxalyl chloride, triethylamine), Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetraoxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $CH_3$—$SiMe_3$ in TBAF with the ketone with the appropriate non-protic solvent at a suitable temperature, yields the 2'-methyl sugar. For example, $CH_3MgBr/TiCl_4$ or $CH_3MgBr/CeCl_3$ can be used as described in Wolfe et al. 1997. *J. Org. Chem.* 62: 1754–1759. The methylated sugar can be optionally protected with a suitable protecting group, preferably with an acyl, substituted alkyl or silyl group, by methods well known to those skilled in the art, as taught by Greene et al. *Protective Groups in Organic Synthesis*, John Wiley and Sons, Second Edition, 1991.

In addition to the above, the 2'-C-substituted sugars used in the synthetic methods described herein are well known in the art and are described, for example, by Sommadossi, et al.[10] and by Carrol, et al.[11,12] all of which are incorporated herein by reference in their entirety.

Scheme 3 below describes the alternative synthesis of a protected sugar that is useful for coupling to the bases described herein.

SCHEME 3

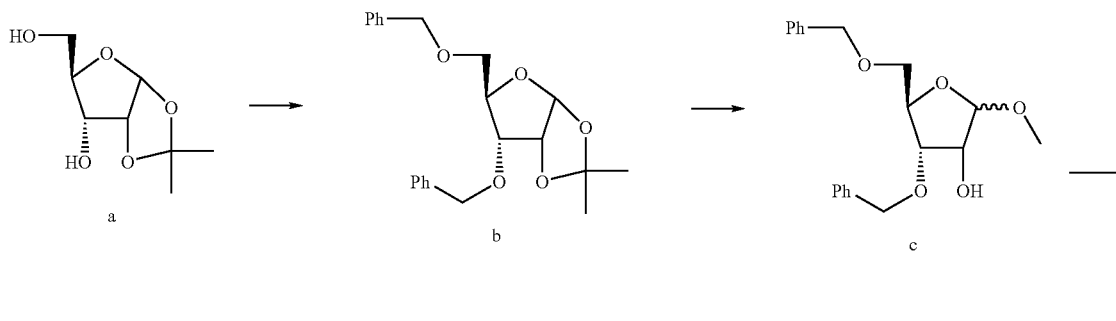

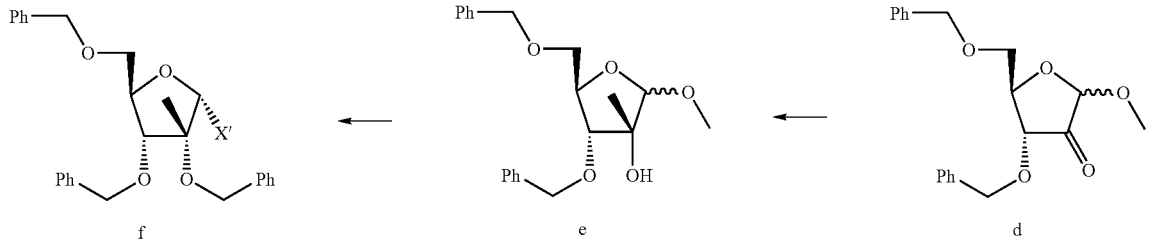

where Ph is phenyl and X' is a suitable leaving group such as halo

Formation of sugar a in Scheme 1, above, is accomplished as described by Mandal, S. B., et al., *Synth. Commun.*, 1993, 9, page 1239, starting from commercial D-ribose. Protection of the hydroxy groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. Sugar e is prepared by using a modification of the Grignard reaction with $CH_3MgBr$ or other appropriate organometallic as described herein (with no titanium/cerium needed). Finally the halogenated sugar (X'=halo) used in the subsequent coupling reaction is prepared using the same protection method as used to make sugar b above. The halogenation is described in Seela, U.S. Pat. No. 6,211,158.

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 4 below.

SCHEME 4

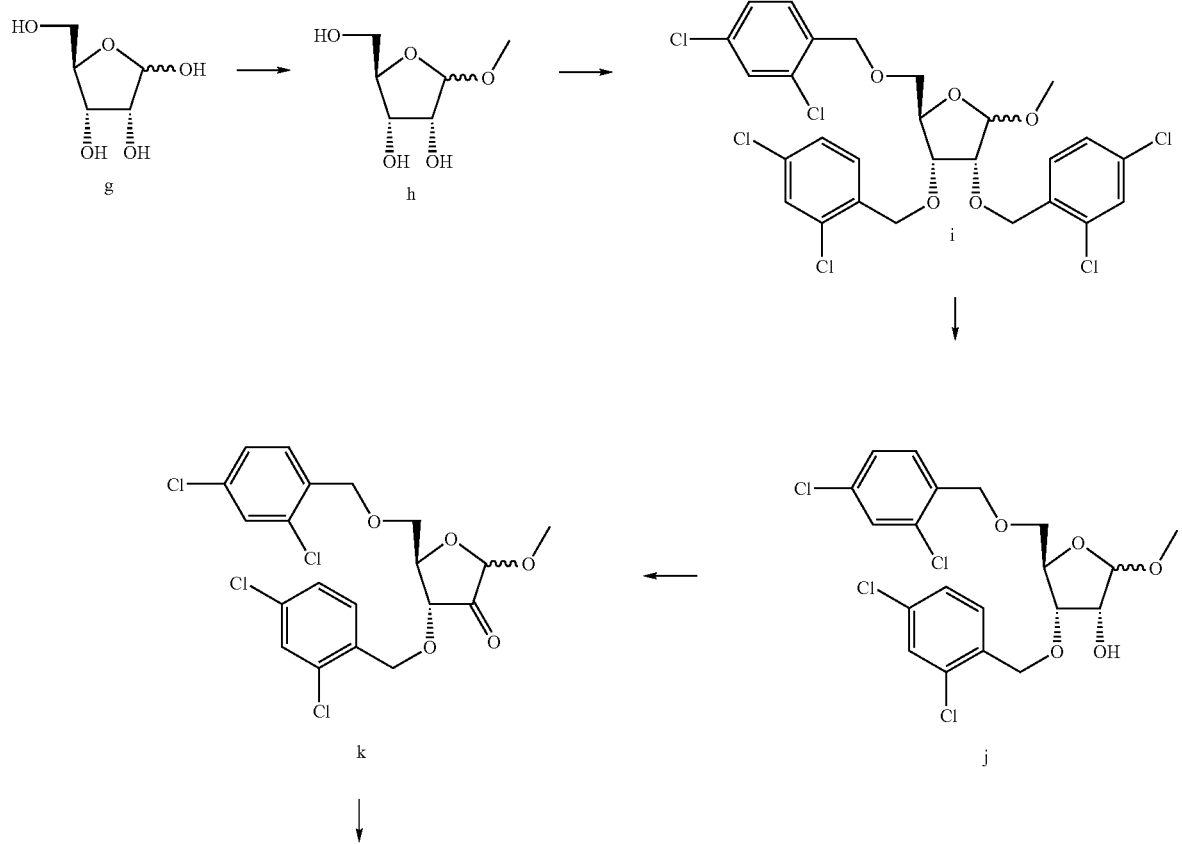

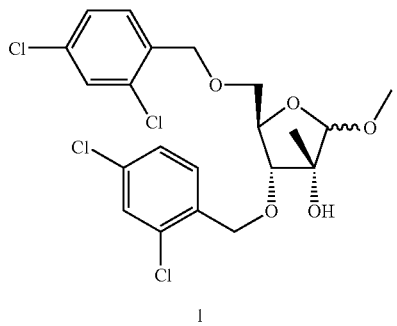

l

In Scheme 4, methylation of the hydroxy group of compound g proceeds via conventional methodology to provide for compound h. The 2, 3 and 5 hydroxy groups of the compound h are each protected with 2,4-dichlorobenzyl groups to provide for compound i. Selective deprotection of the 2-(2',4'-dichlorobenzyl) group on compound i proceeds via contact with stannous chloride in a suitable solvent such as methylene chloride, chloroform, and the like at reduced temperatures, e.g., ~0 to 5° C., until reaction completion, e.g., 24–72 hours provides for compound j. Oxidation of the 2-hydroxy group proceeds as described herein to provide for compound k. Methylation also proceeds as described herein to provide for compound l.

Preparation of compounds where W, $W^1$ or $W^2$ is other than hydrogen, using the compounds prepared as above as the starting materials, can be accomplished using the methods described in the following reviews of prodrug preparation:

1) Cooperwood, J. S. et al., "*Nucleoside and Nucleotide prodrugs*," in Ed(s) Chu, C. K. Recent Advances in Nucleosides (2002), 92–147.
2) Zemlicka, J. et al., Biochimica et Biophysica Acta (2002), 158(2–3), 276–286.
3) Wagner, C. et al., Medicinal Research Reviews (2002), 20(6), 417–451.
4) Meier, C. et al., Synlett (1998), (3), 233–242.

For example, conversion of the 5'-hydroxyl group of the 1-[5-(alkynyl)-4-amino-pyrrolo[2,3-d]pyrimidine]-2'-C-methyl-β-D-ribofuranoside compounds to a phospho, diphospho or triphospho-analog can prepared using the methods describe in D. W. Hutchinson, (Ed. Leroy b. Townsend) "The Synthesis, reaction and Properties of Nucleoside Mono-, Di-, Tri-, and tertaphosphate and Nucleosides with Changes in the Phosphoryl Residue," Chemistry of Nucleosides and Nucleotides, Plenum Press, (1991) 2.

The preparation of amino acid esters on the ribofuranoside can be accomplished as shown in Scheme 5 below:

SCHEME 5

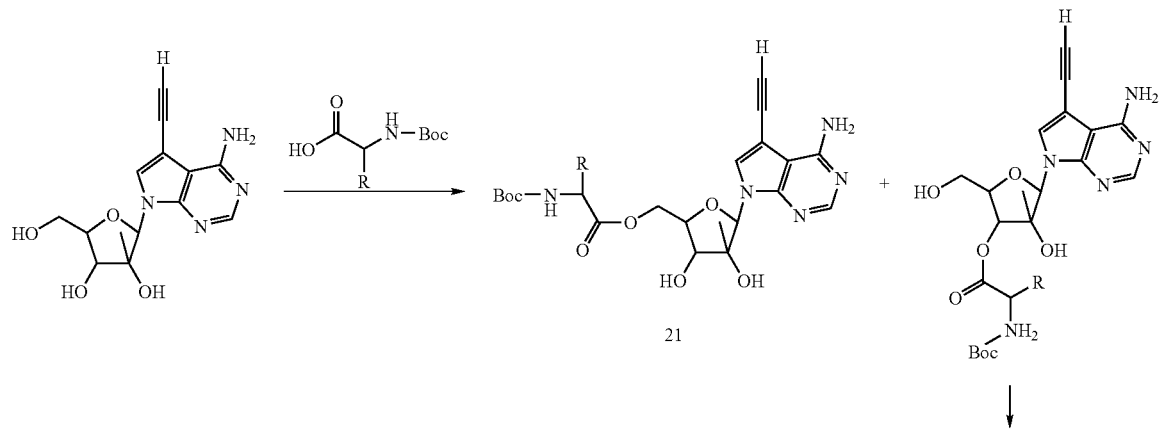

21

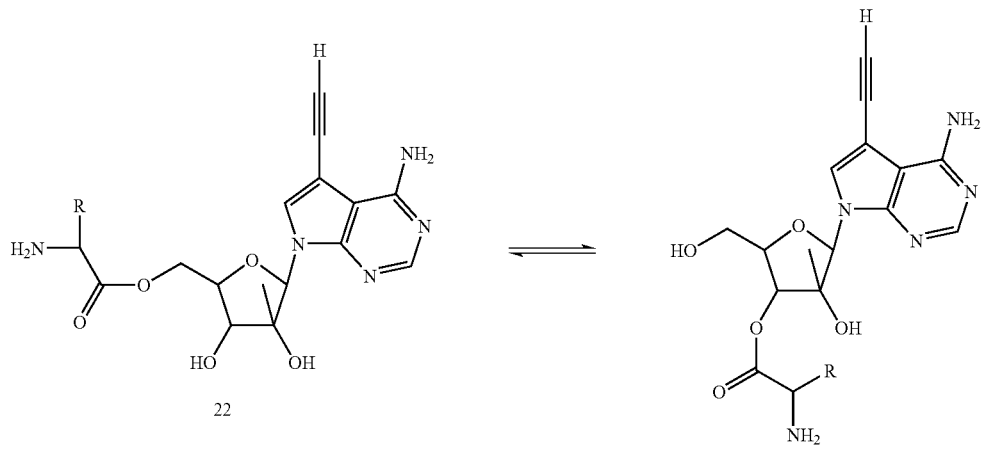

a R = isopropyl
b R = methyl

The desired boc-protected amino acid, (preferably an L-amino acid), and N,N'-carbonyldiimidazole are dissolved in an inert solvent such as THF. The reaction mixture is held between about 20 and about 40° C. for about 0.5 to 24 hours. A solution containing an slight excess of the desired nucleoside in an inert solvent such as DMF, is added to the Boc-protected amino acid mixture and is heated at about 40 to about 80° C. for about 2 to about 24 hours. A mixture of structural isomers is isolated and separated using conventional techniques such as evaporation, precipitation, filtration, crystallization, chromatography and the like.

The desired ester is then acidified using, for example, 1:1 v/v TFA/DCM solution for about 0.1 to about 1 hour about 20 and about 40° C. and evaporated. The residue is dissolved in water and held at about 0 to about 30° C. for about 2 to about 24 hours. The mixture can be separated and the desired product isolated by RP-HPLC using standard techniques and conditions.

While the scheme above demonstrates the production of deazapurine prodrugs, this process can be used on any desired nucleoside compound. Likewise, the amino acid may be protected with any protective group appropriate to the reaction conditions. These protective groups are well known in the art.

The preparation of other alkyl esters on the ribofuranoside can be accomplished as shown in Scheme 6 below:

SCHEME 6

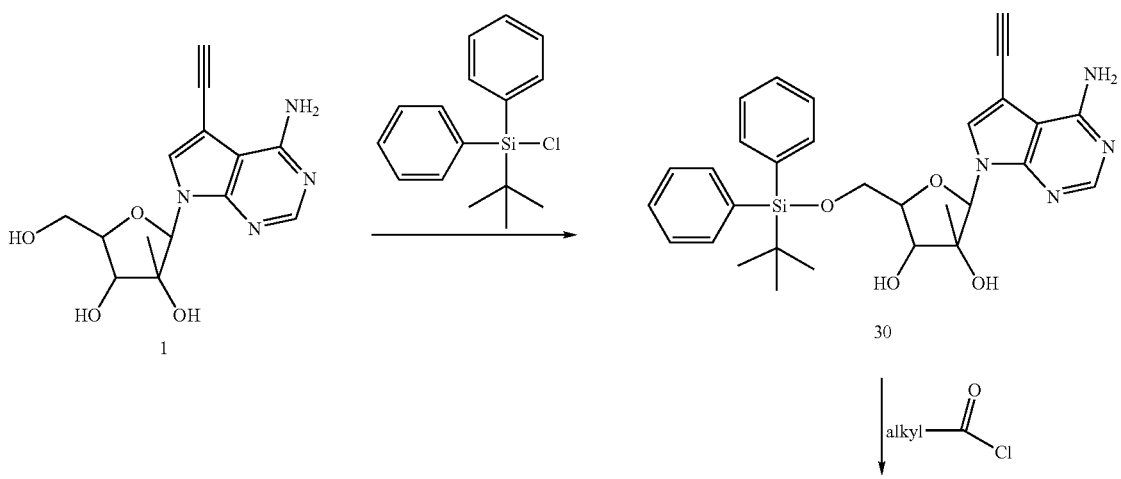

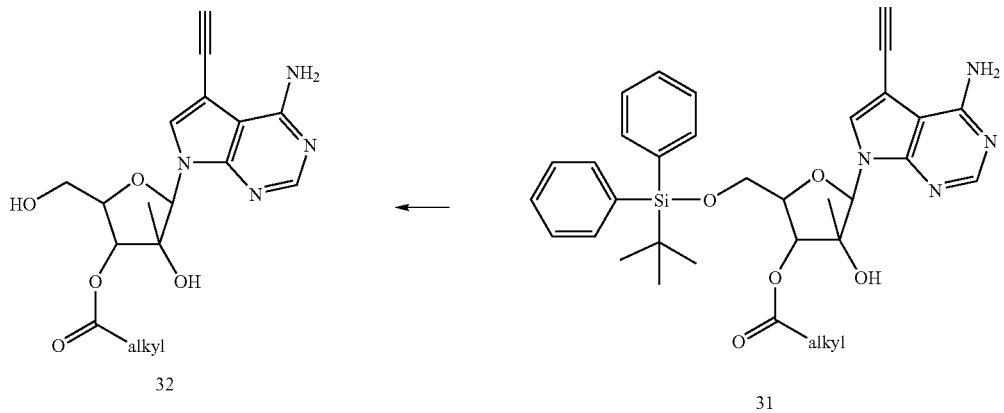

Compound 1 is dissolved in a dry solvent, such as pyridine, and a silylhalide, such as tert-butylchlorodiphenylsilane, is added to form a protecting group at the 5'-position on the sugar. Any protecting group which can be directed to the 5'-position and can be removed orthongally to the final desired 3'-ester can be used. This reaction is run for about 4 to 24 hours at a temperature of about 10 to 40° C. The desired acyl chloride is added to the protected nucleoside, compound 30, and stirred for about 4 to about 24 hours to form compound 31. Which can be isolated and purified using standard techniques such as isolation, crystallization, extraction, filtration, chromatography and the like. Compound 32 is prepared by removing the protecting group at the 5'-position. This can be accomplished by reacting compound 30 with a 1M solution of tetrabutylammonium fluoride in THF. The final product is isolated and purified using standard techniques such as isolation, crystallization, extraction, filtration, chromatography and the like.

While the scheme above demonstrates the production of deazapurine prodrugs, this process can be used on any desired nucleoside compound.

Utility, Testing, and Administration

Utility

The present invention provides novel compounds possessing antiviral activity, including against hepatitis C virus. The compounds of this invention inhibit viral replication by inhibiting the enzymes involved in replication, including RNA dependent RNA polymerase. They may also inhibit other enzymes utilized in the activity or proliferation of viruses in the flaviviridae family, such as HCV.

The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention may be used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula I may range from approximately 0.05 to 50 mg per kilogram body weight of the recipient per day; preferably about 0.01–25 mg/kg/day, more preferably from about 0.5 to 10 mg/kg/day. Thus, for administration to a 70 kg person, the dosage range would most preferably be about 35–70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, or an inhibitor of inosine monophosphate dehydrognease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201–210 (2000).

EXAMPLES

The examples below as well as throughout the application, the following abbreviations have the following meanings. If not defined, the terms have their generally accepted meanings.

| | |
|---|---|
| AcOH or HOAc = | acetic acid |
| $Ac_2O$ = | acetic anhydride |
| Ar = | aryl hydrogen |
| atm = | Atmosphere |
| CAN = | ceric ammonium nitrate |
| bs = | Broad singlet |
| cm = | Centimeter |
| d = | Doublet |
| dd = | doublet of doublets |
| dt = | doublet of triplets |
| DBU = | 1,8-diazabicyclo[5.4.0]undec-7-ene |
| DCB = | 2,4-dichlorobenzyl |
| DCM = | dichloromethane |
| DCC = | dicyclohexylcarbodiimide |
| DMEM = | Delbecco's minimum eagles medium |
| DMF = | dimethylformamide |
| DMSO = | dimethylsulfoxide |
| DTT = | Dithiothreitol |
| EDTA = | ethylene diamine tetraacetic acid |
| Fmoc = | 9-fluorenylmethyl chloroformate |
| eq. or eq = | Equivalents |
| g = | Gram |
| h or hr = | Hour |
| HCV = | hepatitis C virus |
| HPLC = | high performance liquid chromatography |
| IC50 = | Inhibitory concentration at 50% inhibition |
| IPTG = | Isopropyl β-D-1-thiogalactopyranoside |
| IU = | international units |
| kg = | Kilogram |
| L = | Liters |
| m = | Multiplet |
| M = | Molar |
| Me = | Methyl |
| mg = | Milligram |
| min = | minutes |
| mL = | Milliliter |
| mm = | Millimeters |
| mM = | Millimolar |
| mmol = | Millimol |
| MS = | mass spectrum |
| mp = | Melting point |
| ng = | Nanograms |
| nm = | Nanometers |
| nM = | Nanomolar |
| NMR = | nuclear magnetic resonance |
| NTA = | Nitrilotriacetic acid |
| NTP = | nucleotide triphosphate |
| RP HPLC = | reverse phase high performance liquid chromatography |
| s = | Singlet |
| t = | Triplet |
| TBAF = | Tetrabutylammonium fluride |
| TC50 = | Toxic concentration at 50% cell toxicity |
| TEA = | |
| TFA = | Trifluoroacetic acid |
| THF = | tetrahydrofuran |
| Tlc or TLC = | thin layer chromatography |
| UTP = | uridine triphosphate |
| UV = | ultraviolet |
| μL = | Microliters |
| μg = | Micrograms |
| μM = | Micromolar |
| v/v = | volume to volume |
| wt % = | weight percent |

In addition, all reaction and melting temperatures are in degrees Celsius unless reported otherwise and all percentages are molar percents again unless indicated otherwise.

In the examples below as well as elsewhere throughout this application, the claimed compounds employ the following numbering system:

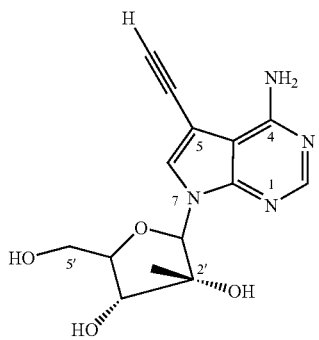

Example 1

Synthesis of the sugar intermediate 1-methoxy-2-methyl-3,5-di-O-(2,4-dichlorobenzyl)-D-ribofuranose (Compound 8)

The title compound was prepared using the methods described in Martin, P.; Helv. Chim. Acta, 1995, 78, 486 and Carroll, et al. International Patent Application WO 02/057287 A2.

Example 2

Preparation of 7-(2'-methyl-β-D-ribofuranosyl)-4-amino-5-(ethyn-1-yl)-pyrrolo[2,3-d]pyrimidine (Compound 1)

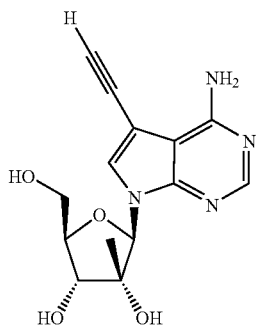

Step 1.
4-Chloro-5-iodo-7H-pyrrolo[2,3-d]pyrimidine (Compound 3)

4-Chloro-7H-pyrrolo[2,3-d]pyrimidine 10.75 g (70 mmol) (Toronto Research Chemicals, Inc) and N-iodosuccinimide (16.8 g, 75 mmol) were dissolved in 400 mL of dry DMF and left at ambient temperature in the darkness over night. The solvent was evaporated. The yellow residue was suspended in hot 10% solution of $Na_2SO_3$, filtered, washed twice with hot water and crystallized from ethanol to yield 14.6 g (74.6%) of the title compound as off-white crystals. The mother liquid was evaporated up to ⅓ volume and crystallized again from ethanol to give 2.47 g (12.3%) of the title product.

Total yield is close to 100%.

M.p. 212–214 (decomposition)

UV $\lambda_{max}$: 307, 266, 230, 227 nm (methanol)

MS: 277.93 (M–H), 313 (M+Cl)

$^1$H-NMR (DMSO-d6): 12.94 (s, 1H, NH), 8.58 (s, 1H, H-2), 7.94 (s, 1H, H-8)

Step 2. 7-(2'-methyl-3',5'-di-O-(2,4-dichlorobenzyl)-β-D-ribofuranosyl)-4-chloro-5-iodo-pyrrolo[2,3-d]pyrimidine (Compound 4)

The base (Compound 3), obtained above, (33.5 g, 120 mmol) was suspended in 1000 mL of $CH_3CN$. NaH was added portionwise (5 g, 125 mmol 60% in oil) and the reaction mixture was stirred at room temperature until NaH was dissolved (about 2 hours). 1-methoxy-2-methyl-3,5-di-O-(2,4-dichlorobenzyl)-D-ribofuranose (Compound 8, see Example 1 above) (33 g, 60 mmol) was dissolved in 1000 mL of DCM and cooled to 4° C. in an ice/water bath. HBr—gas was bubbled through DCM solution for about 30 min. The reaction was monitored by TLC by disappearance of the starting sugar (ether/hexane 9:1 v/v). Upon reaction completion, the solvent was evaporated with a bath temperature not higher that 20° C. and kept for 30 min. in deep vacuum to remove all traces of HBr. A solution of the preformed Na-salt of base 3 was quickly filtered and the filtrate added to the sugar component. The reaction was kept overnight at ambient temperature, then neutralized with HCl/dioxane and evaporated. Toluene (300 mL) was added to form a light tan precipitate of nonreacted heterocyclic base which was filtered off. The filtrate was concentrated to a volume of approximately 150 mL and loaded onto a 2 L glass filter with silica gel. The filter was washed with 1 L of toluene, the product was eluted with 10% ethyl acetate in toluene (about 9 L of solvent). The solvent was evaporated and the residue crystallized from ethanol to yield 27.5 g (55.6%) of titled nucleoside.

M.p. 67–70

$^1$H-NMR (DMSO-d6): 8.66 (s, 1H, H-2), 8.07 (s, 1H, H-8), 7.62–7.34 (m, 6H, dichlorophenyl), 6.22 (s, 1H, H-1'), 5.64 (s, 1H, H-3'), 4.78–4.55 (m, 4H, $CH_2$-benzyl, 2'-OH, H-4'), 4.20 (s, 2H, $CH_2$-benzyl), 3.97–3.93 and 3.78–3.75 (dd, 1H, H-5'), 0.92 (s, 3H, 2'-methyl)

MS: 743.99 (M+H),

Step 3. 7-(2'-methyl-β-D-ribofuranosyl)-4-chloro-5-iodo-pyrrolo[2,3-d]pyrimidine (compound 5)

To a solution of compound 4 from the previous step (27.5 g) in DCM (800 mL) at −70° C. was added boron trichloride (1M in DCM, 400 mL) dropwise. The mixture was stirred at −70° C. for 2.5 hours and additionally overnight at −20° C. The reaction was quenched by addition of methanol/DCM (500 mL, 1:1) and the resulting mixture stirred at −20° C. for 30 min., then neutralized by aqueous ammonia at the same temperature. The solid was filtered and washed 3 times with methanol/DCM (1:1 v/v). The filtrates were combined with 200 mL of silica gel and evaporated up to dryness. The dry residue was distributed between 1500 mL of acetonitrile and 300 mL of hexane. Acetonitrile was collected, extracted 3 times with hexane and evaporated. The residue was dissolved in ethyl acetate (600 mL) and washed 5 times with water, brine, dried over sodium sulfate and evaporated. The residue was purified from small amount of nonreacted base by flash chromatography on silica gel in methanol/acetone 1:2 v/v (about 3 liters). The solvent was evaporated and the residue crystallized from acetone/hexane to give 12.9 g (82%) of the title nucleoside 5.

$^1$H-NMR (DMSO-d6): 8.84 (s, 1H, H-2), 8.20 (s, 1H, H-8), 6.21 (s, 1H, H-1'), 4.00–3.60 (m, sugar), 0.84 (s, 3H, 2'-methyl)

MS: 426.26 (M+H)

M.p. 182–185

Step 4. 7-(2'-methyl-β-D-ribofuranosyl)-4-amino-5-iodo-pyrrolo[2,3-d]pyrimidine (Compound 6)

Nucleoside 5 (1.5 g, 3.5 mmol) prepared above was treated with liquid ammonia at 85° C. for 24 hours in a metal pressure reactor. After evaporation of ammonia, the crude residue was dissolved in methanol, silica gel added (about 20 mL) and concentrated to dryness. The product bearing silica gel was then loaded onto a silica gel column (5×10 cm) in acetone and then eluted, collecting 50 mL fractions. Fractions 2–8 contained the titled compound. Acetone was evaporated and the residue crystallized from methanol/acetonitrile to give 1.2 g (84%) of the titled nucleoside M.p. 220–222 (decompostion)

$^1$H-NMR (DMSO-d6): 8.20 (s, 1H, H-2), 7.80 (s, 1H, H-8), 6.80–6.50 (bs, 2H, NH$_2$), 6.09 (s, 1H, H-1'), 5.19 (t, 1H, sugar), 5.13–5.11 (m, 2H, sugar), 4.00–3.70 (m, 3H, sugar), 3.60–3.20 (m, 1H, sugar), 0.84 (s, 3H, 2'-methyl).

MS 407.32 (M+H).

Step 5. 7-(2'-methyl-β-D-ribofuranosyl)-4-amino-5-(trimethylsilanylethyn-1-yl)-pyrrolo[2,3-d]pyrimidine (Compound 7)

Aminonucleoside 6, synthesized in the previous step, (1.7 g, 4.2 mmol) was dissolved in a mixture of 12 mL dry DMF and 28 mL dry THF. Triethylamine (3.6 mmol, 0.5 mL) and CuI (1 mmol, 80 mg) were added and the flask was filled with argon. Tetrakis(triphenylphosphine)palladium(0) (0.04 mmol, 46 mg) followed finally by (trimethylsilyl)acetylene (1.5 eq.) were added and the mixture was stirred under argon for 20 hours. The solvent was then evaporated, the residue dissolved in acetone and then filtered through silica gel (5×10 cm) on a glass filter funnel. The acetone was evaporated, the residue dissolved in acetonitrile and filtered again through the silica gel column of the same size with elution using acetonitrile. The acetonitrile was concentrated to a small volume, then approx. 10 volumes of ether were added and the solution was sonicated for 5 min. White crystals of the titled compound formed, yielding 0.8 g compound 7 (71%).

M.p. 188–191 (decomposition)

$^1$H-NMR (DMSO-d6): 8.17 (s, 1H, H-2), 7.92 (s, 1H, H-8), 7.20–6.80 (t, 2H, NH$_2$), 5.83 (s, 1H, H-1'), 3.75–3.20 (m, sugar), 0.45 (s, 3H, 2'-methyl), 0 (s, 9H, Si(CH$_3$)$_3$).

Step 6. Preparation of title compound: 7-(2'-methyl-β-D-ribofuranosyl)-4-amino-5-(ethyn-1-yl)-pyrrolo[2,3-d]pyrimidine (Compound 1)

Silylated nucleoside 7 (1 g, 2.6 mmol) was dissolved in 10 mL of methanol, 10 mL of NH$_4$OH was added and the mixture left at ambient temperature for 1 hour. The solvent was evaporated, the residue dissolved in methanol and co-evaporated with silica gel (30 mL). Dry silica was loaded on the glass filter with silica gel (4×6 cm), compound was eluted with acetone. Solvent was evaporated and the residue crystallized from methanol/acetonitrile, yield 0.5 g (62%);

M.p. 209–219 (decomposition);

MS 305.13 (M+H);

$^1$H-NMR (DMSO-d6): 8.10 (s, 1H, H-2), 7.94 (s, 1H, H-8), 6.08 (s, 1H, H-1'), 5.32–5.13 (m, 3H, sugar), 3.96–3.62 (m, 4H, sugar), 0.68 (s, 3H, methyl).

Example 3

Preparation of 7-(2'-methyl-3'-O-L-Valine ester-β-D-ribofuranosyl)-4-amino-5-(ethyn-1-y)-pyrrolo[2,3-d]pyrimidine (22a)

The synthesis of this compound is shown generally in Scheme 5.

Boc-protected L-valine (271 mg, 1.25 mmol) and N,N'-carbonyldiimidazole (203 mg, 1.25 mmol) were dissolved in 5 ml of THF and kept at ambient temperature for 2 hours. A solution of compound 1 (300 mg, 1 mmol) in 5 ml of DMF was added and the mixture was heated at 65° C. overnight. The HPLC analysis of the reaction mixture demonstrated presence of starting nucleoside and the 5'-monoacylated product (compound 21a). The target BocValine derivative (compound 21a) was isolated by preparative RP HPLC from 0 to 100% B, A-0.1% TFA in water, B-0.1% TFA in CH$_3$CN. Yield was 40% (the mixture of two isomers 1:5).

Major isomer:

MS 504 (M+1);

NMR (CD$_3$OD): δ 8.11 & 7.93 (s, 1H, base), 6.23 (s, 1 H, H-1'), 5.44 (d, 1H, H-3'), 4.27 (dt, 1H, H-4'), 4.02–3.96 & 3.75–3.70 (dd, 1H, H-5'a and H-5'b), 3.42 (d, 1H, α-H), 2.21 (m, 1H, β-H), 0.9 (m, 9H, Boc), 0.89 (s, 3H, 2'-CH$_3$).

Minor isomer:

MS 504 (M+1);

NMR (CD$_3$OD): δ 8.92 & 8.10 (s, 1H, base), 6.28 (s, 1H, H-1'), 5.53 (d, 1H, H-3'), 4.32 (dt, 1H, H-4'), 4.10–4.05 & 3.80–3.74 (dd, 1H, H-5'a and H-5'b), 3.43 (d, 1H, α-H), 2.21 (m, 1H, β-H), 1.3–0.9 (m, 15H, Boc & Val-CH$_3$), 0.89 (s, 3H, 2'-CH$_3$).

The ester from the previous step was treated with TFA/DCM 1:1 v/v for 20 min at room temperature and evaporated. The residue was dissolved in water and left at 10° C. overnight. The mixture was separated by RP HPLC from 0 to 100% B, buffers are as described above. Compound with the longest retention time was collected, evaporated and identified as 3'-isomer of nucleoside 22a.

MS 404.14 (M+1);

UV (pH1): 251 nm, 282 nm;

NMR (CD$_3$OD): δ 8.17& 7.87 (s, 1H, base), 6.21 (s, 1H, H-1'), 4.72 (d, 1H, α-H), 4.12–3.82 (m, 4H, sugar), 2.28 (m, 1H, β-H), 1.08 (dd, 6H, Val-CH$_3$), 0.84 (s, 3H, 2'-CH$_3$).

After 3 days of storage in dry conditions or few hours in solution compound was transformed into the mixture of two isomers.

Example 4

Synthesis of 7-(2'-methyl-3'-O-L-alanine ester-β-D-ribofuranosyl)-4-amino-5-(ethyn-1-yl)-pyrrolo[2,3-d]pyrimidine (22b)

Compound 22b was synthesized as described above for 22a using Boc-protected L-alanine;

MS 376.17 (M+1);

NMR (CD$_3$OD): δ 8.61 & 8.28 (s, 1H, base), 6.38 (s, 1H, H-1'), 4.12 (m, 5H, α-H & sugar), 1.71 (d, 3H, Ala-CH$_3$), 1.60 (m, 1H, β-H), 0.85 (s, 3H, 2'-CH$_3$).

After 3 hours of storage in dry conditions or 30 min. stoage in solution compound 22b was transformed into the mixture of two isomers.

Example 5

Synthesis of 7-(2'-methyl-3'-O-trimethyl acetyl ester-β-D-ribofuranosyl)-4-amino-5-(ethyn-1-yl)-pyrrolo[2,3-d]pyrimidine (32 where alkyl is t-butyl)

Compound 1 (150 mg, 0.5 mmol) was dissolved in 10 mL of dry pyridine. tert-Butylchlorodiphenylsilane (274 mL, 1 mmol) was then added and reaction was maintained for 16 hours at room temperature. Trimethylacetyl chloride was added to the reaction mixture (90 µL 0.75 mmol) and the mixture was stirred for 16 hours. The mixture was dissolved in 70 mL of chloroform and extracted with water (30 mL), 10% NaHCO$_3$ (30 mL), dried over Na$_2$SO$_4$, evaporated and co-evaporated with toluene to remove the traces of pyridine. The resulting oil was dissolved in 20 mL of THF and 2 mL of a 1M solution of tetrabutylammonium fluoride in THF was added. In 16 hours the solvent was evaporated, and the resulted oil dissolved in 10 mL of DMF and separated by preparative RP HPLC from 0 to 100% B in 20 min, F=10 ml/min. Column Phenominex 250×20 mm, Synergi 4 u, Hydro PP 80A. Buffer A—water, buffer B—CH$_3$CN. Retention time for target compound was 15 min. Corresponding fractions were collected, evaporated to yield light tan foam.

MS 389.10 (M+1);

H$^1$NMR (DMSO-d6): 8.20 & 7.80 (s, 1H, base), 6.04 (s, 1H, H-1'), 3.92–3.80 (m, 6H, sugar), 3.40 (s, 9H, CH$_3$-acetyl), 0.65 (s, 3H, CH$_3$-2').

Example 6

Synthesis of 7-(2'-methyl-β-D-ribofuranosyl)-4-amino-5-(ethyn-1-yl)-pyrrolo[2,3-d]pyrimidine 5'-triphosphate 7-(2'-methyl-β-D-ribofuranosyl)-4-amino-5-(ethyn-1-yl)-pyrrolo[2,3-d]pyrimidine 5' (0.1 mmol) was co-evaporated 3 times with dry DMF, dissolved in 2 mL of PO(OMe)$_3$, cool to 5° C. and POCl$_3$ (35 µL) and proton sponge (64 mg) were added. The mixture was stirred at 5° C. for 3 h, then tetrabutylammonium pyrophosphate (2 mmol, 4 mL of 0.5M solution in DMF) was added and the mixture was kept for 2 more h at the same temperature. The reaction was quenched with (Et$_3$N)HCO$_3$ buffer (pH 7.5) followed with water. The solvents were evaporated, the residue dissolved in methanol (3 mL) and precipitated with ether (30 mL). The solid residue was purified by ion exchange (IE) HPLC on Vydac column (250×10 mm) 0 to 100% B. Buffer A was 25 mM NaH$_2$PO$_4$/Na$_2$HPO$_4$, pH 3, buffer B was 310 mM NaH$_2$PO$_4$/Na$_2$HPO$_4$, pH 3. The last peak was collected, concentrated up to the volume of 5 mL and repurified on RP HPLC on Phenominex column (250×20 mm) in gradient from 0 to 100% of buffer B in buffer A. Buffer A was 0.5 M aqueous solution of triethylammonium acetate, buffer B was 0.5 M acetonitrile solution of triethylammonium acetate. Fractions containing the title compound were combined, evaporated, co-evaporated 3 times with water and lyophilized from water;

MS: 542.99 (M–H), 270.99 (½M–H);

UV (0.1% TFA) λmax: 212.24, 235.62, 277.98;

$^1$H-NMR: 8.01 & 7.59 (s, 1H each, base), 6.00 (s, 1H, H-1'), 4.32–4.00 (m, 4H, sugar), 3.55 (s, 1H, ethynyl), 0.65 (s, 3H, methyl-2');

$^{31}$P-NMR: –8.60 (d, 1P, P-α), –10.12 (d, 1P, P-γ), –21.42 (t, 1P, P-β).

Example 7

Synthesis of 7-(2'-methyl-β-D-ribofuranosyl)-4-amino-5-(ethyn-1-yl)-pyrrolo[2,3-d]pyrimidine 5'-phosphate 7-(2'-methyl-β-D-ribofuranosyl)-4-amino-5-(ethyn-1-yl)-pyrrolo[2,3-d]pyrimidine 5' (0.1 mmol) was co-evaporated 3 times with dry DMF, dissolved in 2 mL of PO(OMe)$_3$, cool to 5° C. and POCl$_3$ (35 µL) and proton sponge (64 mg) were added. The mixture was stirred at 5° C. for 3 h. The reaction was quenched with (Et$_3$N)HCO$_3$ buffer (pH 7.5) followed with water. The solvents were evaporated, the residue dissolved in methanol (3 mL) and precipitated with ether (30 mL). The solid residue was purified by ion exchange HPLC on Vydac column (250×10 mm) 0 to 100% B. Buffer A was 25 mM NaH$_2$PO$_4$/Na$_2$HPO$_4$, pH 3, buffer B was 310 mM NaH$_2$PO$_4$/Na$_2$HPO$_4$, pH 3. The last peak was collected, concentrated up to the volume of 5 mL and repurified on RP HPLC on Phenominex column (250×20 mm) in gradient from 0 to 100% of buffer B in buffer A. Buffer A was 0.5 M aqueous solution of triethylammonium acetate, buffer B was 0.5 M acetonitrile solution of triethylammonium acetate. Fractions containing the title compound were combined, evaporated, co-evaporated 3 times with water and lyophilized from water;

MS: 384.12 (M–H);

$^1$H-NMR: 7.97 & 7.67 (s, 1H each, base), 6.12 (s, 1H, H-1'), 4.10–3.85 (m, 4H, sugar), 3.15 (s, 1H, ethynyl), 0.87 (s, 3H, methyl-2');

$^{31}$P-NMR: 5.02 (s, 1P).

Comparative Example A

Preparation of 7-(2'-C-methyl-β-D-ribofuranosyl)-4-amino-5-(propyn-1-yl)-pyrrolo[2,3-d]pyrimidine

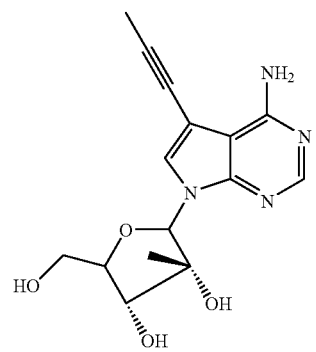

To a solution of the product from Step 4, Example 2 (50.0 mg, 0.123 mmol) in 3.2 mL THF-DMF (2:1 v/v) was added CuI (9.2 mg, 0.048 mmol), TEA (16 µL, 0.113 mmol), tetrakis(triphenylphosphine)palladium(0) (14.0 mg, 0.012 mmol) and the solution degassed with argon. The solution was cooled to 0° C. and propyne gas was bubbled through the solution for 1 min. The reaction was then allowed to slowly warm to room temperature over 4 hours. The procedure of charging reaction with propyne was repeated twice more until no traces of starting material was observed by TLC. The reaction mixture was concentrated in vacuo, taken up in DMF and purified by RP HPLC on Phenominex column (250×20 mm) using gradient of acetonitrile in water from 0 to 50% over 30 min at 10 mL/min to yield 26 mg (66%) of the title compound;

$^1$H-NMR (CD$_3$OD): 8.07 (s, 1H), 7.67 (s, 1H), 6.19 (s, 1H), 4.11–3.84 (m, 4H, sugar), 2.09(s, 3H), 0.82 (s, 3H);

MS: 319.11 (M+H).

Comparative Example B

Preparation of 7-(2'-C-methyl-β-D-ribofuranosyl)-4-amino-5-(butyn-1-yl)-pyrrolo[2,3-d]pyrimidine

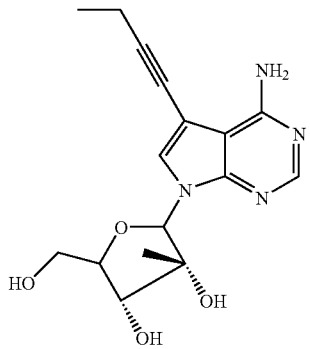

To a solution of the product from Step 4, Example 2 (50.0 mg, 0.123 mmol) in 3.2 mL THF-DMF (2:1 v/v) was added CuI (9.2 mg, 0.048 mmol), TEA (16 μL, 0.113 mmol), tetrakis(triphenylphosphine)palladium(0) (14.0 mg, 0.012 mmol) and the solution degassed with argon. The solution was cooled to 0° C. and butyne gas was bubbled through the solution for 1 min. The reaction was then allowed to slowly warm to room temperature over 4 hours. The reaction mixture was concentrated in vacuo, taken up in DMF and purified by RP HPLC on Phenominex column (250×20 mm) using gradient of acetonitrile in water from 0 to 50% over 30 min at 10 mL/min to yield 13 mg (32%) of the title compound;

$^1$H-NMR (CD$_3$OD): 8.08 (s, 1H), 7.67 (s, 1H), 6.19 (s, 1H), 4.11–3.80 (m, 4H, sugar), 2.48(q, 2H), 1.26 (t, 3H). 0.83 (s, 3H);

MS: 333.13 (M+H).

Comparative Example C

Preparation of 7-(2'-C-methyl-β-D-ribofuranosyl)-4-amino-5-(3-hydroxypropyn-1-yl)-pyrrolo[2,3-d]pyrimidine

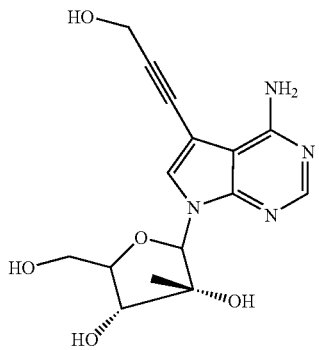

A solution was made of the product from Step 4, Example 2 (50.0 mg, 0.1231 mmol) in 5 mL dimethylformamide. The solution was degassed by bubbling with argon while sonicating for 5 min. To this solution was added triethylamine (16.0 μL, 0.1145 mmol), copper iodide (9.4 mg, 0.0492 mmol), and tetrakis(triphenyl-phosphine)palladium (0) (14.2 mg, 0.0123 mmol). Next, propargyloxytrimethylsilane (113.7 μL, 0.7386 mmol) was added. The mixture was stirred under argon for 4 hours. Upon completion, the mixture was concentrated in vacuo. The reaction crude was dissolved in 1 mL dimethylformamide, diluted to 50 mL with deionized water and then washed through a celite pad. The solution was again concentrated down to dryness, then redissolved in 1.0 mL dimethylformamide and 3.5 mL water. The title compound was purified by HPLC;

$^1$H-NMR (CD$_3$OD): 8.10 (s, 1H), 7.80 (s, 1H), 6.21 (s, 1H), 4.44 (d, 2H), 4.11–3.82 (m, 4H), 0.83 (s, 3H). MS: 335.13 (m/z).

Comparative Example D

Preparation of 7-(2'-C-methyl-β-D-ribofuranosyl)-4-amino-5-(3-aminopropyn-1-yl)-pyrrolo[2,3-d]pyrimidine

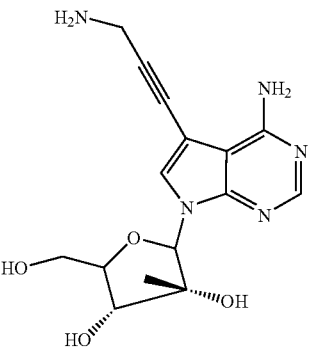

Step 1. Prop-2-ynyl-carbamic acid 9H-fluoren-9-ylmethyl ester

To a solution of propargylamine (250 μL, 3.645 mmol) in diisopropylethylamine (1.273 mL, 7.290 mmol), was added 9-fluorenylmethyl chloroformate (Fmoc), dissolved in 7 mL dimethylformamide. The mixture was stirred under argon overnight at room temperature. After completion, the solution was reduced in vacuo. An ethyl acetate/water extraction procedure was performed to isolate the product; MS: 278.10 (m/z).

Step 2. 7-(2'-C-methyl-β-D-ribofuranosyl)-4-amino-5-(3-aminopropyn-1-yl)-pyrrolo[2,3-d]pyrimidine A solution was made of the product from Step 4, Example 2 (124.5 mg, 0.3065 mmol) in 10 mL dimethylformamide, which was degassed by bubbling with argon while sonicating for 5 min. To this solution was added triethylamine (39.7 μL, 0.2850 mmol), copper iodide (23.5 mg, 0.1226 mmol), and tetrakis(triphenyl-phosphine)palladium (0) (35.4 mg, 0.0307 mmol). Fmoc-propargylamine from Step 1 (465.9 mg, 0.1.680 mmol) was added and the mixture was stirred under argon for 4 h. Upon completion, the mixture was concentrated in vacuo. The reaction crude was dissolved in 1 mL DMF, and then diluted to 50 mL with deionized water and then washed through a celite pad. The solution was evaporated to dryness and redissolved in 1.0 mL DMF and 3.5 mL water. The title compound was purified by HPLC;

$^1$H-NMR (DMF-d$_7$): 8.17 (s, 1H), 8.08 (s, 1H), 6.28 (s, 1H), 5.80–5.32 (m, 3H), 4.19–3.82 (m, 4H), 3.37–3–30 (m, 2H), 0.83 (s, 3H). MS: 334.15 (m/z).

Biological Examples

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73:1649–1654, 1999; Ishii et al., *Hepatology*, 29:1227–1235, 1999; Lohmann et al., *Jnl of Bio. Chem.*, 274:10807–10815, 1999; and Yamashita et al., *Jnl. of Bio. Chem.*, 273:15479–15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on September 1995, describes an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1(Supp 4) 18–24.

Screens that measure reductions in kinase activity from HCV drugs are disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs are disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) is used for screening of compounds of the present invention for HCV RNA dependent RNA polymerase. The ET cell line is stably transfected with RNA transcripts harboring a I$_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells are grown in DMEM, supplemented with 10% fetal calf serum, 2 mM Glutamine, Penicillin (100 IU/mL)/Streptomycin (100 μg/mL), 1× nonessential amino acids, and 250 μg/mL G418 ("Geneticin"). They are all available through Life Technologies (Bethesda, Md.). The cells are plated at 0.5–1.0×10$^4$ cells/well in the 96 well plates and incubated for 24 hrs before adding nucleoside analogs. Then the compounds were added to the cells to achieve a final concentration of 5 or 50 μm. Luciferase activity will be measured 48–72 hours later by adding a lysis buffer and the substrate (Catalog number Glo-lysis buffer E2661 and Bright-Glo leuciferase system E2620 Promega, Madison, Wis.). Cells should not be too confluent during the assay. Percent inhibition of replication will be plotted relative to no compound control. Under the same condition, cytotoxicity of the compounds will be determined using cell proliferation reagent, WST-1 (Roche, Germany). The compounds showing antiviral activities, but no significant cytotoxicities will be chosen to determine IC$_{50}$ and TC$_{50}$. For these determinations, 6 dilutions of each compound were used. Compounds were typically diluted 3 fold to span a concentration range of 250 fold. IC$_{50}$ and TC$_{50}$ values were calculated by fitting % inhibition at each concentration to the following equation:

$$\% \text{ inhibition} = 100\%/[(IC50/[I])^b + 1]$$

where b is Hill's coefficient.

Data for compounds of this invention and for some homologs and analogues of the compounds of this invention are give in Tables II and III below.

TABLE II

| R | HCV Replicon IC$_{50}$ (μM) | HCV Replicon TC$_{50}$ (μM) |
| --- | --- | --- |
| –H | 0.09 | >50 |
| –CH$_3$ | >50 | >50 |
| –CH$_2$CH$_3$ | >50 | >50 |
| –CH$_2$OH | >50 | >50 |
| –CH$_2$NH$_2$ | >50 | >50 |

To form the 5-ethyl nucleoside shown below in Table III, the 5-acetylene nucleoside, compound 1, is hydrogenated using Pd/C in the presence of hydrogen at elevated pressures, preferably in a solvent such methanol.

TABLE III

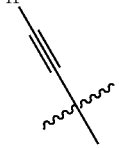

| R | HCV Replicon IC$_{50}$ (μM) | HCV Replicon TC$_{50}$ (μM) |
|---|---|---|
| H | 0.09 | >50 |
| 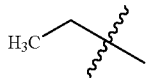 | >50 | >50 |

Example 3

Cloning and Expression of Recombinant HCV-NS5b

The coding sequence of NS5b protein is cloned by PCR from pFKI$_{389}$luc/NS3-3'/ET as described by Lohmann, V., et al. (1999) *Science* 285, 110–113 using the following primers:

```
                                        (SEQ. ID. NO. 1)
aggacatggatccgcggggtcgggcacgagacag (SEQ. ID. NO. 2)
aaggctggcatgcactcaatgtcctacacatggac
```

The cloned fragment is missing the C terminus 21 amino acid residues. The cloned fragment is inserted into an IPTG-inducible expression plasmid that provides an epitope tag (His)6 at the carboxy terminus of the protein.

The recombinant enzyme is expressed in XL-1 cells and after induction of expression, the protein is purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a biotinylated, heteropolymeric template, which includes a portion of the HCV genome. Typically, the assay mixture (50 μL) contains 10 mM Tris-HCl (pH 7.5), 5 mM MgCl$_2$, 0.2 mM EDTA, 10 mM KCl, 1 unit/μL RNAsin, 1 mM DTT, 10 μM each of NTP, including [$^3$H]-UTP, and 10 ng/μL heteropolymeric template. Test compounds are initially dissolved in 100% DMSO and further diluted in aqueous buffer containing 5% DMSO. Typically, compounds are tested at concentrations between 1 nM and 100 μM. Reactions are started with addition of enzyme and allowed to continue at 37° C. for 2 hours. Reactions are quenched with 8 μL of 100 mM EDTA and reaction mixtures (30 μL) are transferred to streptavidin-coated scintillation proximity microtiter plates (FlashPlates) and incubated at 4° C. overnight. Incorporation of radioactivity is determined by scintillation counting.

Formulation Examples

The following are representative pharmaceutical formulations containing a compound of the present invention.

Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |

| Ingredient | Amount |
|---|---|
| colorings | 0.5 mg |
| distilled water | q.s. to 100 mL |

| Ingredient | Amount |
|---|---|
| compound of the invention | 500 mg |
| Witepsol ® H-15 | balance |

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggacatgga tccgcggggt cgggcacgag acag                             34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggctggca tgcactcaat gtcctacaca tggac                            35
```

Example 4

Injectable Formulation

The following ingredients are mixed to form an injectable formulation.

| Ingredient | Amount |
|---|---|
| compound of this invention | 0.2 mg–20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

What is claimed is:

1. A compounds of Formula I:

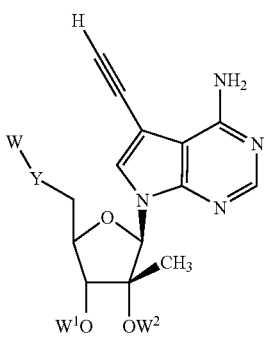

I wherein

Y is selected from the group consisting of a bond, —CH$_2$— or —O—;

each of W, W$^1$ and W$^2$ is independently selected from the group consisting of hydrogen, acyl, oxyacyl, phosphonate, phosphate, phosphate ester, phosphonamidate, phosphorodiamidate, phosphoramidate monoester, cyclic phosphoramidate, cyclic phosphorodiamidate, phosphoramidate diester, and —C(O)CHR$^2$NH$_2$ where R$^2$ is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid; and pharmaceutically acceptable salts or partial salts thereof, wherein substituted alkyl refers to an alkyl group having from 1 to 3 substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

alkoxy refers to alkyl-O—;

substituted alkoxy refers to substituted alkyl-O—;

acyl refers to a moiety selected from the group consisting of alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—;

acylamino refers to —C(O)NR$^4$R$^4$ where each R$^4$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^4$ is joined to form together with the nitrogen atom a heterocyclic or substituted heterocyclic ring;

acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—;

oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—;

substituted alkenyl refers to alkenyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to an unsaturated carbon atom;

substituted alkynyl refers to alkynyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

amino refers to —NH$_2$;

substituted amino refers to NR'R", where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen;

aminoacyl refers to a moiety selected from the group consisting of —NR$^5$C(O)alkyl, —NR$^5$C(O)substituted alkyl, —NR$^5$C(O)cycloalkyl, —NR$^5$C(O)substituted cycloalkyl, —NR$^5$C(O)alkenyl, —NR$^5$C(O)substituted alkenyl, —NR$^5$C(O)alkynyl, —NR$^5$C(O)substituted alkynyl, —NR$^5$C(O)aryl, —NR$^5$C(O)substituted aryl, —NR$^5$C(O)heteroaryl, —NR$^5$C(O)substituted heteroaryl, —NR$^5$C(O)heterocyclic, and —NR$^5$C(O) substituted heterocyclic where R$^5$ is hydrogen or alkyl;

aryl refers to a monovalent aromatic carbocyclic group of from 6 to 14 carbon atoms having a single ring or multiple condensed rings which condensed rings may or may not be aromatic provided that the point of attachment is at an aromatic carbon atom;

substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

aryloxy refers to aryl-O—;

carboxyl refers to —COOH or salts thereof;

carboxyl esters refers to a moiety selected from the group consisting of —C(O)O-alkyl, —C(O)O-substituted alkyl, —C(O)O-aryl, and —C(O)O-substituted aryl;

cycloalkyl refers to a cyclic alkyl group of from 3 to 10 carbon atoms having single or multiple cyclic rings one or more of which may be aromatic or heteroaromatic provided that the point of attachment is through a cycloalkyl ring atom;

substituted cycloalkyl refers to a saturated or unsaturated, but not aromatic, cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

cycloalkoxy refers to —O-cycloalkyl;

substituted cycloalkoxy refers to —O-(substituted cycloalkyl);

formyl refers to HC(O)—;

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur in the ring, wherein the sulfur and nitrogen heteroatoms atoms may also be present in their oxidized forms, such as >N(O), >S(O) and >S(O)$_2$, and wherein the heteroaryl group can have a single ring or multiple condensed rings, wherein the condensed rings may or may not be aromatic and/or contain a heteroatom provided that the point of attachment is through an atom of the aromatic heteroaryl group;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated, but not aromatic, group having a single ring or multiple condensed rings, from 1 to 10 carbon atoms and from 1 to 4 hetero atoms selected from the group consisting of nitrogen, oxygen, sulfur, >S(O), and >S(O)$_2$ within the ring wherein, in fused ring systems, one or more the rings can be cycloalkyl, aryl or heteroaryl provided that the point of attachment is through the heterocyclic ring;

substituted heterocyclyl refers to a heterocyclyl group substituted with from 1 to 3 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

heterocyclyloxy refers to —O-heterocyclic;

substituted heterocyclyloxy refers to —O-(substituted heterocyclic);

phosphate refers to a moiety selected from the group consisting of —OP(O)(OH)$_2$ (monophosphate), —OP(O)(OH)OP(O)(OH)$_2$ (diphosphate) and —OP(O)(OH)OP(O)(OH)OP(O)(OH)$_2$ (triphosphate) or salts thereof, including partial salts thereof;

phosphate ester refers to a mono-, di- or tri-phosphate groups, wherein one or more of the hydroxyl groups is replaced by an alkoxy group;

phosphonate refers to a moiety selected from the group consisting of —OP(O)(R$^6$)(OH), —OP(O)(R$^6$)(OR$^6$) and salts thereof, including partial salts thereof, wherein each R$^6$ is independently selected from hydrogen, alkyl, substituted alkyl, carboxyl, and carboxyl ester;

phosphorodiamidate refers to

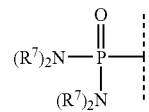

where each R$^7$ may be the same or different and each is hydrogen, alkyl, substituted alkyl, cycloalkyl, or substituted cycloalkyl;

phosphoramidate monoester refers to

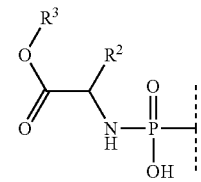

where R$^2$ is selected from the group consisiting of hydrogen, alkyl, substituted alkyl, aryl, substituted aryl, cycloalkyl, substituted cycloalkyl, heteroaryl, substituted hetereoaryl, heterocyclic, substituted heterocyclic, and a sidechain of an amino acid, and R$^3$ is hydrogen or alkyl;

phosphoramidate diester refers to

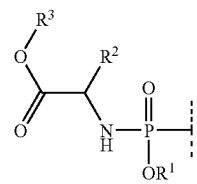

where R$^1$ is selected from the group consisting of alkyl, substututited alkyl, aryl, substituted aryl, cycloalkyl, substituted cycloalkyl, heteroaryl, substituted heteroaryl, heterocyclic and substituted heterocyclic, R$^2$ is selected from the group consisiting of hydrogen, alkyl, substituted alkyl, aryl, substituted aryl, cycloalkyl, substituted cycloalkyl, heteroaryl, substituted hetereoaryl, heterocyclic, substituted heterocyclic, and a sidechain of an amino acid, and R$^3$ is hydrogen or alkyl;

cyclic phosphoramidate refers to

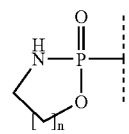

where n is 1 to 3;

cyclic phosphorodiamidate refers to

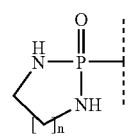

where n is 1 to 3;

phosphonamidate refers to

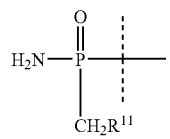

where $R^{11}$ is hydrogen, alkyl, substituted alkyl, cycloalkyl, or substituted cycloalkyl;

thiol refers to —SH;

thioalkyl refers to —S-alkyl;

substituted thioalkyl refers to —S-(substituted alkyl);

thiocycloalkyl refers to —S-cycloalkyl;

substituted thiocycloalkyl refers to —S-(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclic refers to —S-heterocyclic; and substituted thioheterocyclic refers to —S-(substituted heterocyclic).

2. The compound of claim 1 wherein Y is oxygen.

3. The compound of claim 1 wherein W is hydrogen, or $W^1$ is hydrogen, or $W^2$ is hydrogen.

4. The compound of claim 1 wherein W and $W^1$ are hydrogen, or W and $W^2$ are hydrogen, or $W^1$ and $W^2$ are hydrogen.

5. The compound of claim 1 wherein W, $W^1$ and $W^2$ are hydrogen.

6. The compound of claim 4 wherein $W^1$ and $W^2$ are hydrogen and W is hydrogen, acyl, oxyacyl, phosphonate, phosphate ester, phosphate, phosphonamidate, phosphorodiamidate, phosphoramidate monoester, cyclic phosphoramidate, cyclic phosphorodiamidate, phosphoramidate diester, and —C(O)CHR²NH₂ where $R^2$ is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid.

7. The compound of claim 6 wherein $W^1$ and $W^2$ are hydrogen and W is represented by the formula:

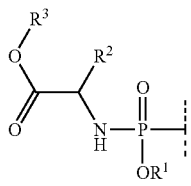

where $R^2$ is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid;

$R^3$ is hydrogen or alkyl; and $R^1$ is selected from the group consisting of alkyl, substituted alkyl, aryl, substituted aryl, cycloalkyl, substituted cycloalkyl, heteroaryl, substituted heteroaryl, heterocyclyl and substituted heterocyclyl.

8. The compound of claim 4 wherein W and $W^2$ are hydrogen and $W^1$ is represented by the formula:

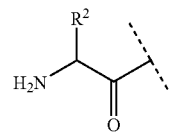

where $R^2$ is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid.

9. A compound of Formula II:

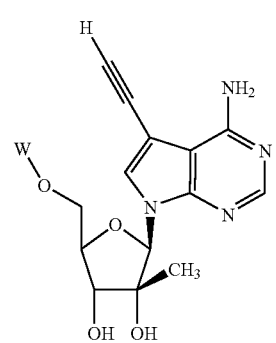

II wherein

W is selected from the group consisting of hydrogen, acyl, oxyacyl, phosphonate, phosphate, phosphate ester, phosphonamidate, phosphorodiamidate, phosphoramidate monoester, cyclic phosphoramidate, cyclic phosphorodiamidate, phosphoramidate diester, and —C(O)CHR₂NH₂ where $R^2$ is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid;

or pharmaceutically acceptable salts or partial salts thereof, wherein substituted alkyl refers to an alkyl group having from 1 to 3 substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic;

alkoxy refers to alkyl-O—;

substituted alkoxy refers to substituted alkyl-O—;

acyl refers to a moiety selected from the group consisting of alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—;

acylamino refers to —C(O)NR⁴R⁴ where each R⁴ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R⁴ is joined to form together with the nitrogen atom a heterocyclic or substituted heterocyclic ring;

acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—;

oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—;

substituted alkenyl refers to alkenyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to an unsaturated carbon atom;

substituted alkynyl refers to alkynyl groups having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

amino refers to —NH₂;

substituted amino refers to —NR'R", where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen;

aminoacyl refers to a moiety selected from the group consisting of —NR⁵C(O)alkyl, —NR⁵C(O)substituted alkyl, —NR⁵C(O)cycloalkyl, —NR⁵C(O)substituted cycloalkyl, —NR⁵C(O)alkenyl, —NR⁵C(O)substituted alkenyl, —NR⁵C(O)alkynyl, —NR⁵C(O)substituted alkynyl, —NR⁵C(O)aryl, —NR⁵C(O)substituted aryl, —NR⁵C(O)heteroaryl, —NR⁵C(O)substituted heteroaryl, —NR⁵C(O)heterocyclic, and —NR⁵C(O) substituted heterocyclic where R⁵ is hydrogen or alkyl;

aryl refers to a monovalent aromatic carbocyclic group of from 6 to 14 carbon atoms having a single ring or multiple condensed rings which condensed rings may or may not be aromatic provided that the point of attachment is at an aromatic carbon atom;

substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

aryloxy refers to aryl-O—;

carboxyl refers to —COOH or salts thereof;

carboxyl esters refers to a moiety selected from the group consisting of —C(O)O-alkyl, —C(O)O-substituted alkyl, —C(O)O-aryl, and —C(O)O-substituted aryl;

cycloalkyl refers to a cyclic alkyl group of from 3 to 10 carbon atoms having single or multiple cyclic rings one or more of which may be aromatic or heteroaromatic provided that the point of attachment is through a cycloalkyl ring atom;

substituted cycloalkyl refers to a saturated or unsaturated, but not aromatic, cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

cycloalkoxy refers to —O-cycloalkyl;

substituted cycloalkoxy refers to —O-(substituted cycloalkyl);

formyl refers to HC(O)—;

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur in the ring, wherein the sulfur and nitrogen heteroatoms atoms may also be present in their oxidized forms, such as >N(O), >S(O) and >S(O)₂, and wherein the heteroaryl group can have a single ring or multiple condensed rings, wherein the condensed rings may or may not be aromatic and/or contain a heteroatom provided that the point of attachment is through an atom of the aromatic heteroaryl group;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated, but not aromatic, group having a single ring or multiple condensed rings, from 1 to 10 carbon atoms and from 1 to 4 hetero atoms selected from the group consisting of nitrogen, oxygen, sulfur, >S(O), and >S(O)$_2$ within the ring wherein, in fused ring systems, one or more the rings can be cycloalkyl, aryl or heteroaryl provided that the point of attachment is through the heterocyclic ring;

substituted heterocyclyl refers to a heterocyclyl group substituted with from 1 to 3 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic;

heterocyclyloxy refers to —O-heterocyclic;

substituted heterocyclyloxy refers to —O-(substituted heterocyclic);

phosphate refers to a moiety selected from the group consisting of —OP(O)(OH)$_2$ (monophosphate), —OP(O)(OH)OP(O)(OH)$_2$ (diphosphate) and —OP(O)(OH)OP(O)(OH)OP(O)(OH)$_2$ (triphosphate) or salts thereof, including partial salts thereof;

phosphate ester refers to a mono-, di- or tri-phosphate groups, wherein one or more of the hydroxyl groups is replaced by an alkoxy group;

phosphonate refers to a moiety selected from the group consisting of OP(O)(R$^6$)(OH), —OP(O)(R$^6$)(OR$^6$) and salts thereof, including partial salts thereof, wherein each R$^6$ is independently selected from hydrogen, alkyl, substituted alkyl, carboxyl, and carboxyl ester;

phosphorodiamidate refers to

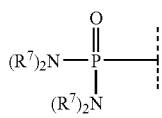

where each R$^7$ may be the same or different and each is hydrogen, alkyl, substituted alkyl, cycloalkyl, or substituted cycloalkyl;

phosphoramidate monoester refers to

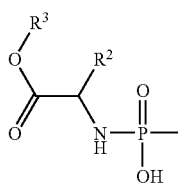

where R$^2$ is selected from the group consisting of hydrogen, alkyl, substituted alkyl, aryl, substituted aryl, cycloalkyl, substituted cycloalkyl, heteroaryl, substituted hetereoaryl, heterocyclic, substituted heterocyclic, and a sidechain of an amino acid, and R$^3$ is hydrogen or alkyl;

phosphoramidate diester refers to

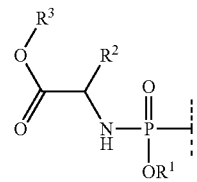

where R$^1$ is selected from the group consisting of alkyl, substutituted alkyl, aryl, substituted aryl, cycloalkyl, substituted cycloalkyl, heteroaryl, substituted heteroaryl, heterocyclic and substituted heterocyclic, R$^2$ is selected from the group consisiting of hydrogen, alkyl, substituted alkyl, aryl, substituted aryl, cycloalkyl, substituted cycloalkyl, heteroaryl, substituted hetereoaryl, heterocyclic, substituted heterocyclic, and a sidechain of an amino acid, and R$^3$ is hydrogen or alkyl;

cyclic phosphoramidate refers to

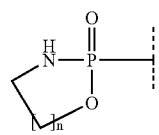

where n is 1 to 3;

cyclic phosphorodiamidate refers to

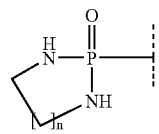

where n is 1 to 3;

phosphonamidate refers to

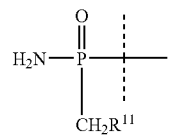

where R$^{11}$ is hydrogen, alkyl, substituted alkyl, cycloalkyl, or substituted cycloalkykyl;

thiol refers to —SH;

thioalkyl refers to —S-alkyl;

substituted thioalkyl refers to —S-(substituted alkyl);

thiocycloalkyl refers to —S-cycloalkyl;

substituted thiocycloalkyl refers to —S-(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclic refers to —S-heterocyclic; and
substituted thioheterocyclic refers to —S-(substituted heterocyclic).

10. The compound of claim 9 wherein W is represented by the formula:

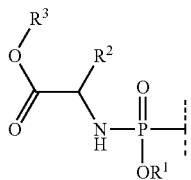

where R² is selected from the group consisting of hydrogen, alkyl, substituted alkyl, aryl, substituted aryl, cycloalkyl, substituted cycloalkyl, heteroaryl, substituted hetereoaryl, heterocyclyl, substituted heterocyclyl, and a sidechain of an amino acid;

R³ is hydrogen or alkyl; and

R¹ is selected from the group consisting of alkyl, substutituted alkyl, aryl, substituted aryl, cycloalkyl, substituted cycloalkyl, heteroaryl, substituted heteroaryl, heterocyclyl and substituted heterocyclyl.

11. 7-(2'-C-methyl-β-D-ribofuranosyl)-4-amino-5-(ethyn-1-yl)-pyrrolo[2,3-d]pyrimidine or pharmaceutically acceptable salts or partial salts thereof.

12. 7-(2'-C-methyl-5'-phospho-β-D-ribofuranosyl)-4-amino-5-(ethyn-1-yl)-pyrrolo[2,3-d]pyrimidine or pharmaceutically acceptable salts or partial salts thereof.

13. 7-(2'-C-methyl-5'-diphospho-β-D-ribofuranosyl)-4-amino-5-[ethyn-1-yl]-pyrrolo[2,3-d]pyrimidine or pharmaceutically acceptable salts or partial salts thereof.

14. 7-(2'-C-methyl-5'-triphospho-β-D-ribofuranosyl)-4-amino-5-(ethyn-1-yl)-pyrrolo[2,3-d]pyrimidine or pharmaceutically acceptable salts or partial salts thereof.

15. 7-(2'-methyl-5'-(phenoxy-L-alaninyl)phosphate-β-D-ribofuranosyl)-4-amino-5-(ethyn-1-yl)-pyrrolo[2,3-d]pyrimidine or pharmaceutically acceptable salts or partial salts thereof.

16. 7-(2'-methyl-3'-O-L-valine ester-β-D-ribofuranosyl)-4-amino-5-(ethyn-1-yl)-pyrrolo[2,3-d]pyrimidine or pharmaceutically acceptable salts or partial salts thereof.

17. 7-(2'-methyl-3'-O-L-alanine ester-β-D-ribofuranosyl)-4-amino-5-(ethyn-1-yl)-pyrrolo[2,3-d]pyrimidine or pharmaceutically acceptable salts or partial salts thereof.

18. A pharmaceutical composition comprising a pharmaceutically acceptable diluent and a therapeutically effective amount of a compound as defined in any one of claims 1, 2, 3 to 9 and 10 to 17.

19. A method for treating and/or inhibiting a viral infection in a mammal in need thereof which infection is mediated at least in part by hepatitis C virus which method comprise administering to said mammal, that has been diagnosed with said viral infection or is at risk of developing said viral infection, a pharmaceutical composition according to claim 18.

* * * * *

UNITED STATES PATENT AND TRADEMARK OFFICE
CERTIFICATE OF CORRECTION

| | | |
|---|---|---|
| PATENT NO. | : 7,157,434 B2 | Page 1 of 1 |
| APPLICATION NO. | : 10/970321 | |
| DATED | : January 2, 2007 | |
| INVENTOR(S) | : Jesse D. Keicher, Christopher D. Roberts and Natalia B. Dyatkina | |

It is certified that error appears in the above-identified patent and that said Letters Patent is hereby corrected as shown below:

Column 58, line 56, replace "cycloalkykyl" with --cycloalkyl--.

Signed and Sealed this

Sixth Day of March, 2007

JON W. DUDAS
*Director of the United States Patent and Trademark Office*